(12) United States Patent
Daniels et al.

(10) Patent No.: US 12,035,206 B2
(45) Date of Patent: Jul. 9, 2024

(54) FABRIC, CONNECTIONS AND FUNCTIONAL STRUCTURES FOR WEARABLE ELECTRONIC GARMENTS AND APPLICATIONS FOR THE SAME

(71) Applicant: Kinaptic, LLC, Madison, CT (US)

(72) Inventors: John J Daniels, Madison, CT (US); Joseph A. Curcio, Grey, ME (US)

( * ) Notice: Subject to any disclaimer, the term of this patent is extended or adjusted under 35 U.S.C. 154(b) by 883 days.

(21) Appl. No.: 16/737,055

(22) Filed: Jan. 8, 2020

(65) Prior Publication Data
US 2020/0237031 A1 Jul. 30, 2020

Related U.S. Application Data

(60) Provisional application No. 62/791,845, filed on Jan. 13, 2019.

(51) Int. Cl.
*A41D 1/00* (2018.01)
*A61B 5/00* (2006.01)
(Continued)

(52) U.S. Cl.
CPC .............. *H04W 4/33* (2018.02); *A41D 1/005* (2013.01); *A61B 5/02055* (2013.01); *A61B 5/6804* (2013.01); *A63B 24/0062* (2013.01); *D03D 1/0088* (2013.01); *D03D 13/004* (2013.01); *D03D 15/00* (2013.01); *G01S 1/024* (2013.01); *G01S 5/021* (2013.01); *G09B 19/0038* (2013.01); *H04W 4/029* (2018.02); *H04W 4/185* (2013.01); *H04W 4/80* (2018.02);
(Continued)

(58) Field of Classification Search
CPC .............. A61B 5/02438; A61B 5/6804; A63B 24/0062
See application file for complete search history.

(56) References Cited

U.S. PATENT DOCUMENTS 6,411,276 B1  6/2002  Braun et al.
6,609,018 B2  8/2003  Cory et al.
(Continued)

FOREIGN PATENT DOCUMENTS

EP  2378956 A2  10/2011
EP  2801389 A1  11/2014
(Continued)

OTHER PUBLICATIONS

China National Intellectual Property Admininstration, First Office Action, Wearable Electric, Multi-Sensory, Human/Machine, Human/Human Interfaces, Mar. 2, 2021, Beijing, China.
(Continued)

*Primary Examiner* — Rex R Holmes
*Assistant Examiner* — Jennifer L Ghand

(57) ABSTRACT

A wearable electronic fabric comprises a woven fabric formed from a plurality of interlaced threads. The plurality of interlaced threads comprise a plurality of warp threads interlaced with a plurality of weft threads. The woven fabric has a top face and a bottom face. A plurality of conductive threads is included among the plurality of interlaced threads at predetermined intervals and interlacing angles to provide a pattern of connection locations. The connection locations are located at regular intervals on at least one of the top face and the bottom face of the woven fabric.

19 Claims, 28 Drawing Sheets

(51) Int. Cl.

| | |
|---|---|
| *A61B 5/0205* | (2006.01) |
| *A63B 24/00* | (2006.01) |
| *D03D 1/00* | (2006.01) |
| *D03D 13/00* | (2006.01) |
| *D03D 15/00* | (2021.01) |
| *G01S 1/02* | (2010.01) |
| *G01S 5/02* | (2010.01) |
| *G09B 19/00* | (2006.01) |
| *H04W 4/029* | (2018.01) |
| *H04W 4/18* | (2009.01) |
| *H04W 4/33* | (2018.01) |
| *H04W 4/80* | (2018.01) |
| *H04W 64/00* | (2009.01) |
| *A41B 1/08* | (2006.01) |
| *A41D 1/084* | (2018.01) |
| *A41D 1/089* | (2018.01) |
| *A61B 5/024* | (2006.01) |
| *A61B 5/08* | (2006.01) |
| *A61B 5/11* | (2006.01) |
| *A61B 5/145* | (2006.01) |
| *A61B 5/389* | (2021.01) |
| *A63F 13/212* | (2014.01) |
| *A63F 13/285* | (2014.01) |

(52) U.S. Cl.
CPC ............ *H04W 64/00* (2013.01); *A41B 1/08* (2013.01); *A41D 1/084* (2013.01); *A41D 1/089* (2018.01); *A61B 5/02438* (2013.01); *A61B 5/08* (2013.01); *A61B 5/11* (2013.01); *A61B 5/14517* (2013.01); *A61B 5/389* (2021.01); *A63B 2024/0096* (2013.01); *A63F 13/212* (2014.09); *A63F 13/285* (2014.09); *A63F 2300/1012* (2013.01); *A63F 2300/1037* (2013.01); *A63F 2300/8082* (2013.01)

(56) References Cited

U.S. PATENT DOCUMENTS

| | | | |
|---|---|---|---|
| 6,892,098 | B2 | 5/2005 | Ayal et al. |
| 6,930,590 | B2 | 8/2005 | Ling et al. |
| 6,965,842 | B2 | 11/2005 | Rekimoto |
| 7,013,179 | B2 | 3/2006 | Carter et al. |
| 7,228,178 | B2 | 6/2007 | Carroll et al. |
| 7,539,724 | B1 | 5/2009 | Callaghan |
| 8,378,964 | B2 | 2/2013 | Ullrich et al. |
| 8,552,847 | B1 | 10/2013 | Hill |
| 8,620,434 | B2 | 12/2013 | Bodlaender et al. |
| 9,390,630 | B2 | 7/2016 | Daniels |
| 10,437,335 | B2 | 10/2019 | Daniels |
| 2003/0068053 | A1 | 4/2003 | Chu |
| 2003/0149457 | A1 | 8/2003 | Tcheng et al. |
| 2003/0170602 | A1 | 9/2003 | Hagita et al. |
| 2004/0057176 | A1* | 3/2004 | Dhawan ................ H05K 3/10 361/62 |
| 2004/0174431 | A1 | 9/2004 | Stienstra |
| 2004/0244564 | A1 | 12/2004 | McGregor |
| 2006/0137511 | A1 | 6/2006 | McGregor |
| 2007/0000374 | A1 | 1/2007 | Clark et al. |
| 2007/0250119 | A1 | 10/2007 | Tyler et al. |
| 2007/0282228 | A1 | 12/2007 | Einav et al. |
| 2008/0103639 | A1 | 5/2008 | Troy et al. |
| 2009/0053683 | A1 | 2/2009 | Brown et al. |
| 2009/0231276 | A1 | 9/2009 | Ullrich et al. |
| 2009/0326406 | A1 | 12/2009 | Tan et al. |
| 2010/0106044 | A1 | 4/2010 | Linderman |
| 2011/0048213 | A1 | 3/2011 | Choi et al. |
| 2011/0094306 | A1* | 4/2011 | Bratkovski ............ G01L 5/228 73/849 |
| 2011/0238079 | A1 | 9/2011 | Hannaford et al. |
| 2012/0035513 | A1 | 2/2012 | Afshar |
| 2012/0094263 | A1 | 4/2012 | Seitz |
| 2012/0167747 | A1 | 7/2012 | Luchinskiy |
| 2012/0216666 | A1 | 8/2012 | Fresolone |
| 2012/0260789 | A1 | 10/2012 | Ur et al. |
| 2013/0029791 | A1 | 1/2013 | Rose et al. |
| 2013/0118339 | A1 | 5/2013 | Lee et al. |
| 2013/0207890 | A1 | 8/2013 | Young |
| 2013/0310122 | A1 | 11/2013 | Piccionielli |
| 2014/0038139 | A1 | 2/2014 | AlDossary |
| 2014/0186810 | A1 | 7/2014 | Falash et al. |
| 2014/0208204 | A1 | 7/2014 | Lacroix et al. |
| 2014/0240103 | A1 | 8/2014 | Lake et al. |
| 2014/0248594 | A1 | 9/2014 | Navas |
| 2014/0282105 | A1 | 9/2014 | Nordstrom |
| 2015/0024381 | A1 | 1/2015 | Zurakowski |
| 2015/0050623 | A1 | 2/2015 | Falash et al. |
| 2015/0140528 | A1 | 5/2015 | Sikstrom et al. |
| 2015/0140529 | A1 | 5/2015 | Tinjust |
| 2015/0221230 | A1 | 8/2015 | Karadjian et al. |
| 2015/0269863 | A1 | 9/2015 | Shrewsbury |
| 2015/0279238 | A1 | 10/2015 | Forte et al. |
| 2015/0294585 | A1 | 10/2015 | Kullok et al. |
| 2015/0294597 | A1 | 10/2015 | Rizzo |
| 2015/0302763 | A1 | 10/2015 | Gleim et al. |
| 2015/0314195 | A1 | 11/2015 | Bekri |
| 2015/0317910 | A1 | 11/2015 | Daniels |
| 2015/0323993 | A1 | 11/2015 | Levesque et al. |
| 2016/0030751 | A1 | 2/2016 | Ghosh et al. |
| 2017/0056644 | A1* | 3/2017 | Chahine ............ A61N 1/36014 |
| 2017/0358235 | A1 | 12/2017 | Daniels |
| 2017/0370030 | A1* | 12/2017 | Podhajny ............... G06F 3/0446 |
| 2018/0303383 | A1* | 10/2018 | Connor ................... G06F 3/014 |
| 2019/0136423 | A1* | 5/2019 | Podhajny ............... D03D 41/00 |
| 2020/0155069 | A1* | 5/2020 | Bogdanovich ....... A61B 5/0002 |

FOREIGN PATENT DOCUMENTS

| | | |
|---|---|---|
| EP | 3544495 | 10/2019 |
| WO | 2010082993 | 7/2010 |
| WO | 2013/071307 A1 | 5/2013 |
| WO | 2014/038049 A1 | 3/2014 |
| WO | 2014113813 A1 | 7/2014 |
| WO | 2016168117 | 10/2016 |
| WO | 2018098046 | 5/2018 |
| WO | 2018098046 A2 | 5/2018 |

OTHER PUBLICATIONS

PCT Search Report for Application No. PCT/US19/045429, dated Dec. 3, 2019 (12 pages).

European Search Report for Application No. 17875007-1122/3544495, dated Jul. 17, 2020 (8 pages).

Robotics and Autonomous System, vol. 63, Part 3, Jan. 2015, pp. 244-252. (Reference cited on U.S. Pat. No. 10,437,335, Issued on Oct. 8, 2019).

Michele Folgheraiter, Giuseppina Gini-Dario Vercesi, J Intel Robot Syst DOI 10.1007/s10846-008-9226-5 Aug. 2008, vol. 52, Issue 3, pp. 465-488. Found at: https://link.springer.corn/article/10.1007/sl0846-008-9226-5. (Reference cited on U.S. Pat. No. 10,437,335, Issued on Oct. 8, 2019.).

\* cited by examiner resistance is dependent on angle, user weight, gps data (kinetic energy), speed real-world view player's VR view

Wearable Electronic Sweat Chemistry Sensor

Isolated View

Screen Printed Sweat Flow-through Structure

1) Backside of Etched Flex Circuit 2) Form Sweat Transfer Aperture

3) Screen Print Hydrophobic Field 4) Screen Print Hydrophilic Channels

Wicking and Evaporation bulk increased by waistband
Figure 45
Wicking/Evaporation Material
Moisture Barrier
Comfortable band against skin
ultra-long service before saturation
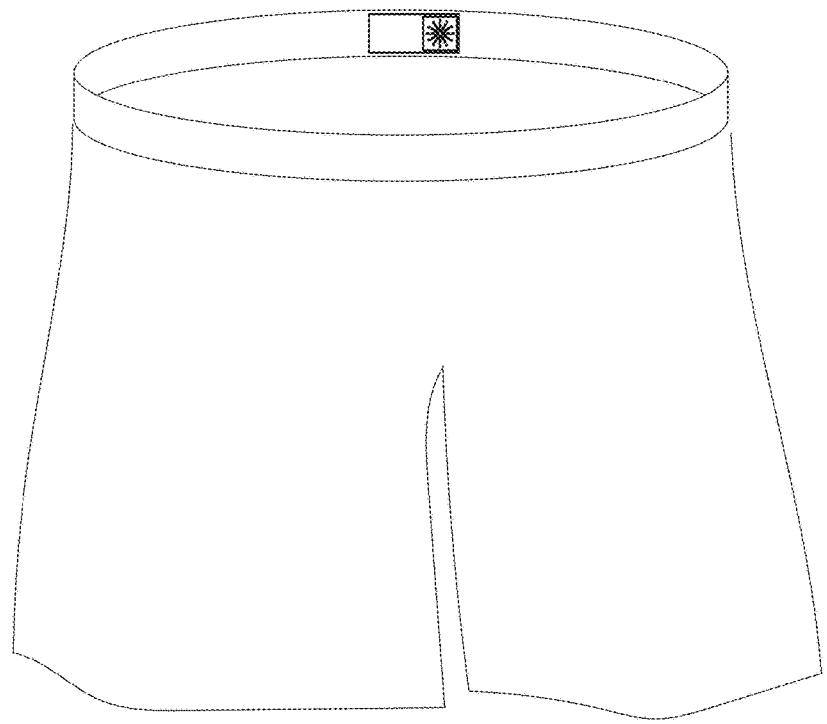
Figure 46

US 12,035,206 B2

FABRIC, CONNECTIONS AND FUNCTIONAL STRUCTURES FOR WEARABLE ELECTRONIC GARMENTS AND APPLICATIONS FOR THE SAME

TECHNICAL FIELD

The exemplary and non-limiting embodiments of this invention relate generally to wireless communication systems, methods, devices and computer programs and, more specifically, relate to functional fabrics used for wearable electronic garments.

The present invention relates to manufacturing methods for forming constituent parts of devices, and a method, apparatus and computer program code for providing, accelerated learning, entertainment and/or cognitive or physical therapy using augmented and/or virtual reality, comprising combined sensory cues, including, but not limited to, haptic, auditory and visual stimulation.

The present invention pertains to a device architecture, specific-use applications, and a high yield manufacturing process for wearable electronics in the form of clothing and other wearable garments with the capability to "detect, analyze and apply" the naturally occurring electrical signals of the human body. More particularly, the present invention pertains to wearable electronics for, among other things, educational, entertainment, gaming, remote unmanned vehicle control, medical and military uses.

The present invention also relates to a method, apparatus and computer program code for providing accelerated learning, entertainment and/or cognitive or physical therapy using augmented and/or virtual reality, comprising combined sensory cues, including, but not limited to, haptic, auditory and visual stimulation.

The present invention also relates to a remote reality ("remotality") interface between humans and machines, and between humans and humans. More particularly, the present invention pertains to a wearable Haptic Human/Machine Interface (HHMI) for uses including, but not limited to, mitigating tremor, accelerated learning, cognitive therapy, remote robotic, drone and probe control and sensing, virtual and augmented reality, stroke, brain and spinal cord rehabilitation, gaming, education, pain relief, entertainment, remote surgery, remote participation in and/or observation of an event such as a sporting event, and biofeedback.

BACKGROUND

This section is intended to provide a background or context to the exemplary embodiments of the invention as recited in the claims. The description herein may include concepts that could be pursued but are not necessarily ones that have been previously conceived, implemented or described. Therefore, unless otherwise indicated herein, what is described in this section is not prior art to the description and claims in this application and is not admitted to be prior art by inclusion in this section.

The desire for wearable computing, where a computer/human interface is always ready for use because it is worn like clothing, has been around for decades. Now, due in large part to Moore's Law and the continuous miniaturization of electronics, and other technologies, such as small, lightweight, ultrahigh-resolution displays, the decades-long vision for Humanistic Intelligence and wearable computing will soon be as common place as the ubiquitous cellphone.

Virtual Reality may be defined as a computer-generated simulation of a three-dimensional image or environment that can be interacted with in a seemingly real or physical way by a user using special electronic equipment, such as goggles, headphones and gloves fitted with sensory cue transducers.

Augmented reality is a live, direct or indirect, view of a physical, real-world environment whose elements are augmented by computer-generated sensory input such as sound, video, graphics or GPS data. It is related to a more general concept called mediated reality, in which a view of reality is modified (possibly even diminished rather than augmented) by a computer. As a result, the technology functions by enhancing one's current perception of reality. By contrast, virtual reality replaces the real world with a simulated one.

Electroencephalography (EEG) is the recording of electrical activity along the scalp. EEG measures voltage fluctuations resulting from ionic current flows within the neurons of the brain. Derivatives of the EEG technique include evoked potentials (EP), which involves averaging the EEG activity time-locked to the presentation of a stimulus of some sort (visual, somatosensory, or auditory). Event-related potentials (ERPs) refer to averaged EEG responses that are timelocked to more complex processing of stimuli; this technique is used in cognitive science, cognitive psychology, and psychophysiological research.

An evoked potential or evoked response is an electrical potential recorded from the nervous system following presentation of a stimulus, as distinct from spontaneous potentials as detected by electroencephalography (EEG), electromyography (EMG), or other electrophysiological recording method. Signals can be recorded from cerebral cortex, brain stem, spinal cord and peripheral nerves. Sensory evoked potentials (SEP) are recorded from the central nervous system following stimulation of sense organs (for example, visual evoked potentials elicited by a flashing light or changing pattern on a monitor; auditory evoked potentials by a click or tone stimulus presented through earphones) or by haptic or somatosensory evoked potential (SSEP) elicited by haptic or electrical stimulation of a sensory or mixed nerve in the periphery. There are three kinds of evoked potentials in widespread clinical use: auditory evoked potentials, usually recorded from the scalp but originating at brainstem level; visual evoked potentials, and somatosensory evoked potentials, which are elicited by electrical stimulation of peripheral nerve.

An event-related potential (ERP) is the measured brain response that is the direct result of a specific sensory, cognitive, or motor event. More formally, it is any stereotyped electrophysiological response to a stimulus. The study of the brain in this way provides a noninvasive means of evaluating brain functioning in patients with cognitive diseases.

Weaving is a method of textile production where threads are interlaced at right angles to form a fabric. The longitudinal threads are called the warp and the lateral threads are the weft. Fabric is typically woven on a loom by holding the warp threads in place while filling threads (the weft) are woven through them. A woven fabric is typically made by interlacing two or more threads at right (and other) angles to one another. Other methods can be used to create a woven fabric including tablet weaving, back-strap, or other techniques with or without using looms. The weave of a fabric is determined by the way the warp and weft threads interlace with each other.

Fashion may change, the composition of fabrics may advance from natural materials such as wool and cotton to synthetics such as nylon and polyester, but the functionality of clothing is still basically the same today as has been for thousands of years. But soon, the function of the garments we wear may dramatically change.

There is a coming revolution in how the clothes we wear that will go far beyond merely covering up the body and providing protection from the elements. Recent advances in fiber materials and manufacturing processes are now allowing for the design of fabrics and functional elements that can detect information, communicate data, store and convert energy, control temperature, change color, etc.

Recent breakthroughs in fiber materials and manufacturing processes have allowed design and production of advanced functional fabrics. These technologies will likely create high-value added products that may reinvigorate US textile manufacturing and usher in an information-based industry that advances at the pace of other digital technologies such as computers and cellular communications. Researchers are beginning to change how traditional fibers, yarns, and fabrics can be designed for use in networked and electronically functional garments, which are a form of wearable electronics. For example, researchers are developing fibers that have the functionality of semiconductor materials.

However, manufacturing fabrics with advanced capabilities requires new materials and methods used, for example, to weave threads into cloth. There is an unmet need for a generalized functional fabric that can be modified and used for a variety of new applications including detecting, analyzing and applying electrical signals to/from the body, detecting sweat chemistry and other biometric information, and providing other features for applications such as communications, health, entertainment, and safety.

SUMMARY

The below summary section is intended to be merely exemplary and non-limiting.

The foregoing and other problems are overcome, and other advantages are realized, by the use of the exemplary embodiments of this invention.

In one exemplary embodiment of the invention, a wearable electronic fabric comprises a woven fabric formed from a plurality of interlaced threads. The plurality of interlaced threads comprise a plurality of warp threads interlaced with a plurality of weft threads. The woven fabric has a top face and a bottom face. A plurality of conductive threads is included among the plurality of interlaced threads at predetermined intervals and interlacing angles to provide a pattern of connection locations. The connection locations are located at regular intervals on at least one of the top face and the bottom face of the woven fabric.

In accordance with another aspect of the invention, an inventive method includes detecting non-biometric data detecting at least one of a position of a bicycle relative to a fixed geographic location, selected gears, and ambient and environmental data. Biometric data is detected detecting at least one biometric signal from a rider of the bicycle, the at least one biometric signal including at least on of EMG, body position, heart rate, sweat chemistry, body temperature, and respiration. The detected non-biometric data and the detected biometric data is recorded. Computer-controlled first sensory cues are generated dependent on at least one of the recorded non-biometric data and biometric data. The first sensory cues are applied to a user. A plurality of visual sensory cues are generated capable of being displayed to the user on a video display device. The visual sensory cues are effective for stimulating a visual processing area of the brain of the user synchronized with the first sensory cues. The visual processing area is stimulated with a visual sensory cue in synchronization with the first sensory cue stimulating the first processing area. The synchronized stimulation of the first processing area and the visual processing area is effective for building up muscle memory to strengthen the user's brain and nervous functions that control the change in the position of the at least one body part.

In accordance with another aspect of the invention, an apparatus, comprises: one or more processors; and one or more memories including computer program code, the one or more memories and the computer program code configured, with the one or more processors, to cause the apparatus to perform at least the following: detecting non-biometric data detecting at least one of a position of a bicycle relative to a fixed geographic location, selected gears, and ambient and environmental data; detecting biometric data detecting at least one biometric signal from a rider of the bicycle, the at least one biometric signal including at least on of EMG, body position, heart rate, sweat chemistry, body temperature, and respiration; recording the detected non-biometric data and the detected biometric data; generating computer-controlled first sensory cues dependent on at least one of the recorded non-biometric data and biometric data; applying the first sensory cues to a user; and generating a plurality of visual sensory cues capable of being displayed to the user on a video display device, the visual sensory cues being effective for stimulating a visual processing area of the brain of the user synchronized with the first sensory cues so that the visual processing area is stimulated with a visual sensory cue in synchronization with the first sensory cue stimulating the first processing area, wherein the synchronized stimulation of the first processing area and the visual processing area is effective for building up muscle memory to strengthen the user's brain and nervous functions that control the change in the position of the at least one body part.

In accordance with another aspect of the invention a computer program product comprises a computer-readable storage medium bearing computer program code embodied therein for use with a computer, the computer program code comprising: code for detecting non-biometric data detecting at least one of a position of a bicycle relative to a fixed geographic location, selected gears, and ambient and environmental data; code for detecting biometric data detecting at least one biometric signal from a rider of the bicycle, the at least one biometric signal including at least on of EMG, body position, heart rate, sweat chemistry, body temperature, and respiration; code for recording the detected non-biometric data and the detected biometric data; code for generating computer-controlled first sensory cues dependent on at least one of the recorded non-biometric data and biometric data; code for applying the first sensory cues to a user; and code for generating a plurality of visual sensory cues capable of being displayed to the user on a video display device, the visual sensory cues being effective for stimulating a visual processing area of the brain of the user synchronized with the first sensory cues so that the visual processing area is stimulated with a visual sensory cue in synchronization with the first sensory cue stimulating the first processing area, wherein the synchronized stimulation of the first processing area and the visual processing area is effective for building up muscle memory to strengthen the user's brain and nervous functions that control the change in the position of the at least one body part.

BRIEF DESCRIPTION OF THE DRAWINGS

The foregoing and other aspects of exemplary embodiments of this invention are made more evident in the following Detailed Description, when read in conjunction with the attached Drawing Figures, wherein:

FIG. 45 shows a side view of the waistband shown in FIG. 46; and FIG. 46 illustrates an inventive wearable electronic garment having a sweat chemistry sensor and a long service before saturation waistband.

DETAILED DESCRIPTION

Below are provided further descriptions of various non-limiting, exemplary embodiments. The exemplary embodiments of the invention, such as those described immediately below, may be implemented, practiced or utilized in any combination (e.g., any combination that is suitable, practicable and/or feasible) and are not limited only to those combinations described herein and/or included in the appended claims.

Figure 1:
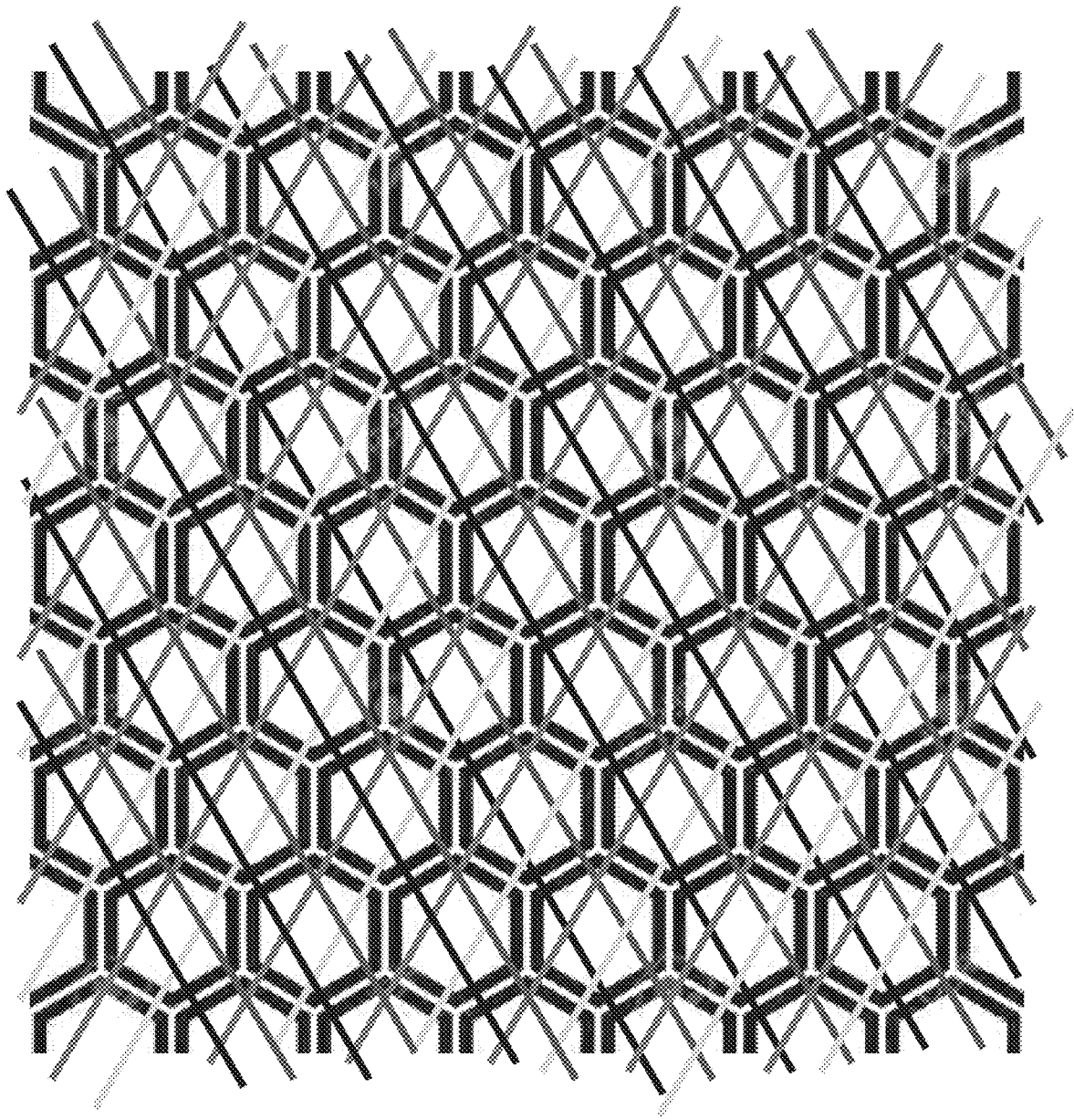
FIG. 1 shows an embodiment of the inventive functional fabric having four conductor wires woven directly into fabric.
Figure 2:
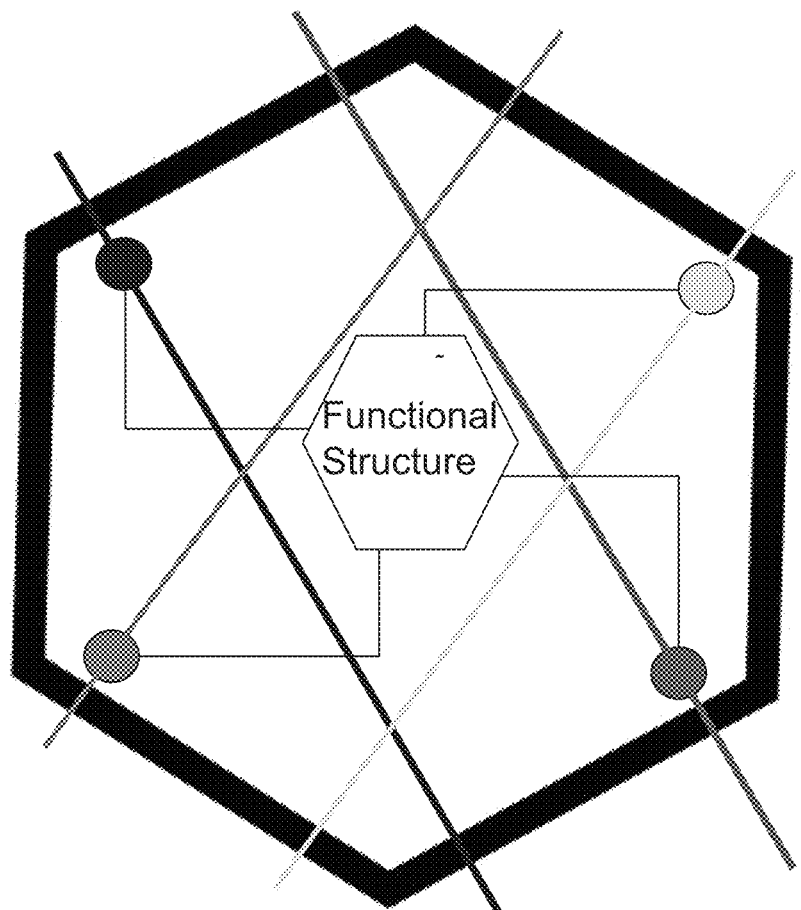
FIG. 2 shows an isolated view of one hexagonal connection element having four connection locations separately connectable with a corresponding conductor wire.

FIG. 1 shows an embodiment of the inventive functional fabric having four conductor wires woven directly into fabric. FIG. 2 shows an isolated view of one hexagonal connection element having four connection locations separately connectable with a corresponding conductor wire. In accordance with an embodiment of the present invention, a wearable electronic fabric comprises a woven fabric formed from a plurality of interlaced threads. The plurality of interlaced threads comprise a plurality of warp threads interlaced with a plurality of weft threads. The woven fabric has a top face and a bottom face. A plurality of conductive threads is included among the plurality of interlaced threads at predetermined intervals and interlacing angles to provide a pattern of connection locations. The connection locations are located at regular intervals on at least one of the top face and the bottom face of the woven fabric.

By weaving four distinct wires along the warp and weft of the fabric, a nano-usb layout of hexagonally shaped pixels can be distributed throughout the fabric itself. Similar to internet-of-things devices and other devices that use, for example, Universal Serial Bus (USB) data transfer, every pixel can have a unique ID and can receive power/ground and data pair for communication to an onboard hub. Each pixel may get electrical contact to the USB bus by being heat staked at the appropriate intersections with the appropriate wires that pass by. The wiring may be woven into the fabric, so they will have 3-D shape and periodically any given wire will appear at a top layer position that is aligned with the "pad" at each pixel, allowing for electrical connection between the wire and the pixel.

Within each pixel, traces that connect with or are connected to function structures are macro-printed using a screen print, inkjet, or the like. Alternatively, or additionally, all or portions of the traces and/or functional structures can be nano-printed, for example, using the technique shown in PCT patent application of Busnaina, et al., PCT/US2008/012977, filed 2008 Nov. 21 US patent, or U.S. Pat. No. 7,799,369 B2, of John J. Daniels, issued 2010 Sep. 21. As another alternative, all or parts of the functional structures may pre-formed, packaged devices, solution processed and deposited in-situ organic and inorganic electronic devices, or bare die electronic devices. The traces will bring all of the electrical connections to the circuit within the pixel.

Figure 5:
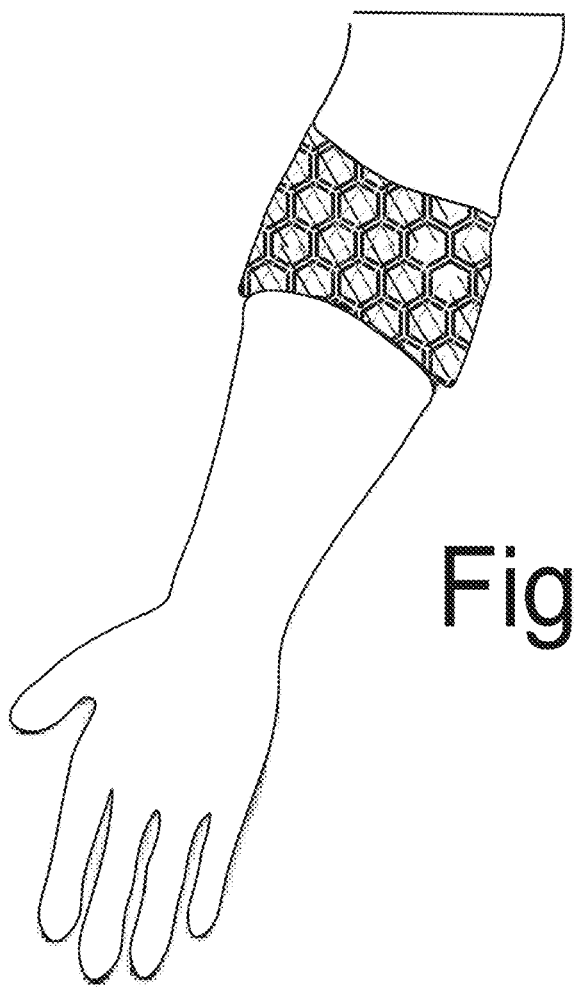
FIG. 5 illustrates a wearable electronic forearm sleeve formed from the inventive functional fabric.
Figure 6:
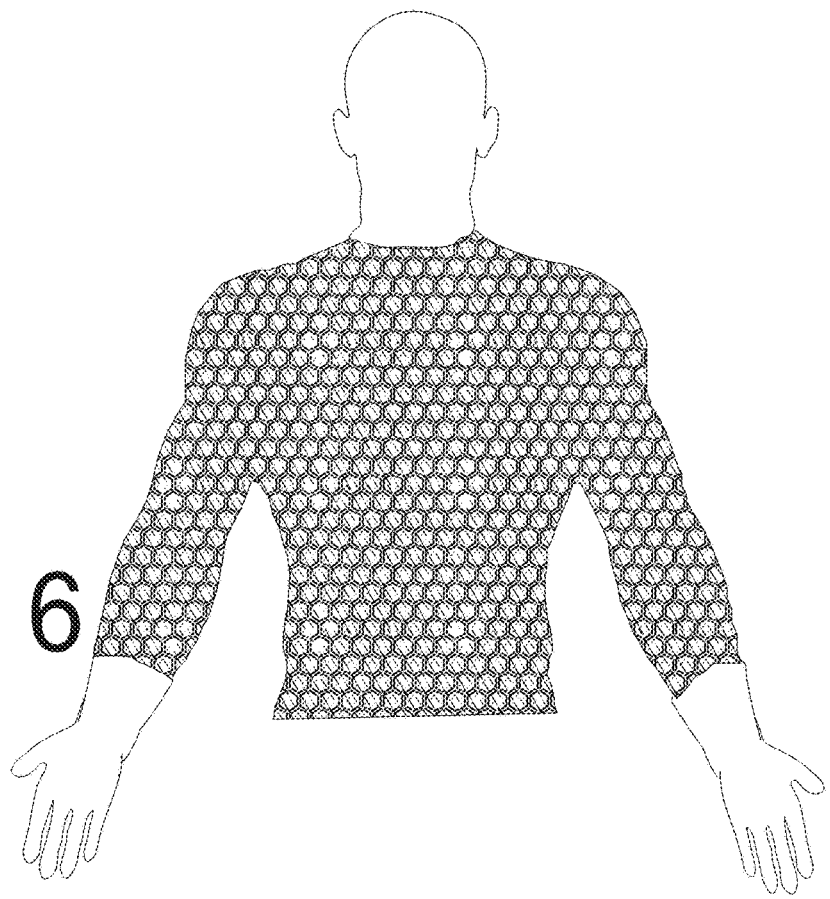
FIG. 6 illustrates a wearable electronic torso shirt formed from the inventive functional fabric.

FIG. 5 illustrates a wearable electronic forearm sleeve formed from the inventive functional fabric. FIG. 6 illustrates a wearable electronic torso shirt formed from the inventive functional fabric. In FIGS. 5 and 6 the top face of the woven fabric is shown. Not shown is the bottom face which is against the skin of the user. On the bottom face the pattern of interlaced conductive and non-conductive threads enable a connection of a functional element, such as a bio-detector or a transcutaneous electrical nerve stimulation electrode at the connection locations. Each connection location may be individually addressed, for example, by scanning the power and ground wires.

Figure 7:
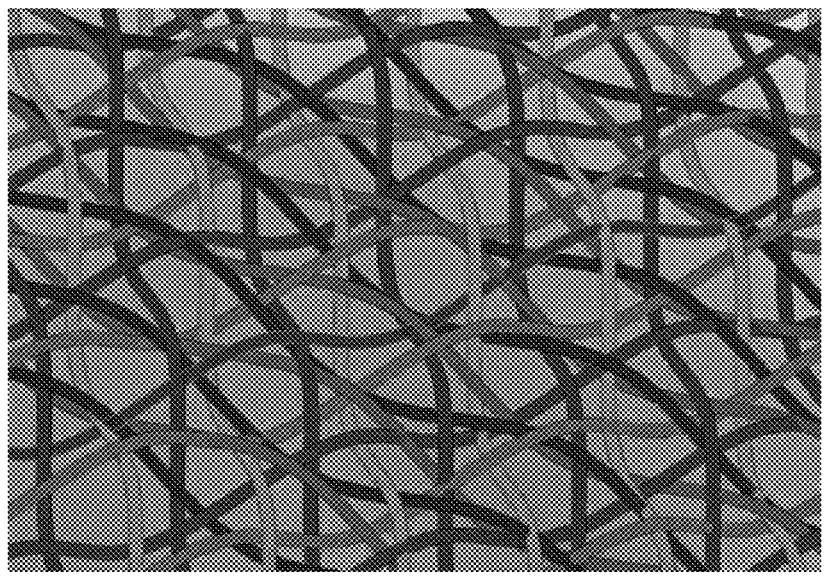
FIG. 7 illustrates an example of a six-conductor weave for incorporating into fabric.
Figure 8:
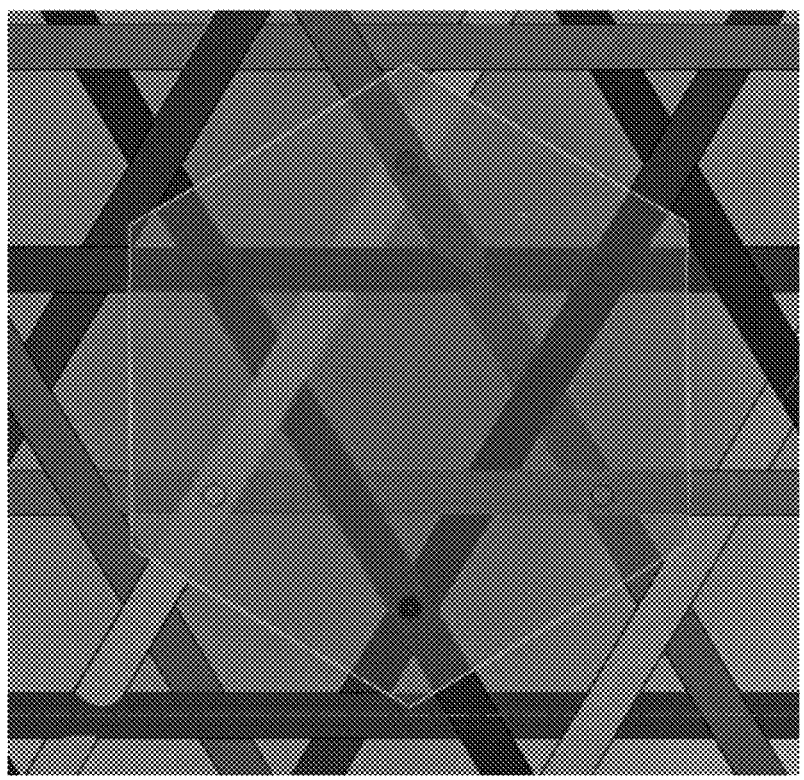
FIG. 8 illustrates a single hexagon connection element (semi-transparent to facilitate viewing) for connecting with the six-conductor weave.

FIG. 7 illustrates an example of a six-conductor weave for incorporating into fabric. FIG. 8 illustrates a single hexagon connection element (semi-transparent to facilitate viewing) for connecting with the six-conductor weave. The red and black wires depict power (+ and −) and the yellow and green wires depict signal pair (data positive and data negative). The purple and blue wires depict AC and/or alternate signal or power as may be required. For example, using TENS/EMS, purple and blue could be used for AC TENS signal, switched locally through addressable interface (as described in text). This 4-wire pattern follows the USB standard (typically using white wire as data positive but shown in yellow here for visibility on page). A single HEX interface pad shown as semi-transparent to aid in viewing the contact pins that protrude from lower surface of pad to provide electrical interface to wires woven into cloth below.

The conductive threads may be insulated with a conductive core. The conductive threads may include at least one conductive thread having a semiconductor composition. The plurality of conductive threads may be interlaced in the warp threads and the weave threads so that at the regular intervals a connection area is disposed having first conductive thread, a second conductive thread, a third conductive thread and a fourth through sixth conductive thread. The first conductive thread may provide a ground connection portion, the second conductive thread a power connection portion, the third conductive thread a data-in connection portion and the fourth conductive thread a data-out connection portion. The fifth and sixth conductive threads may provide additional power and/or signal input and output to/from the connection element and the conductive threads woven into the fabric, or conductive traces printed onto the fabric.

Figure 3:
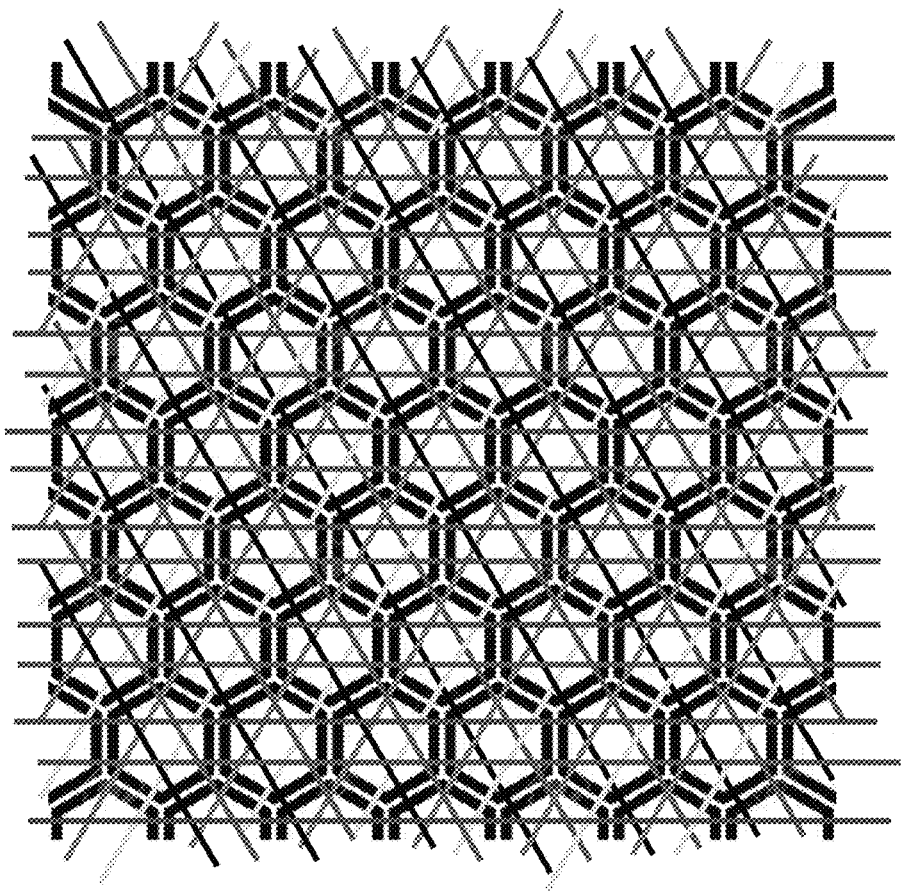
FIG. 3 shows an embodiment of the inventive functional fabric having with six conductor wires integrated woven directly into fabric.
Figure 4:
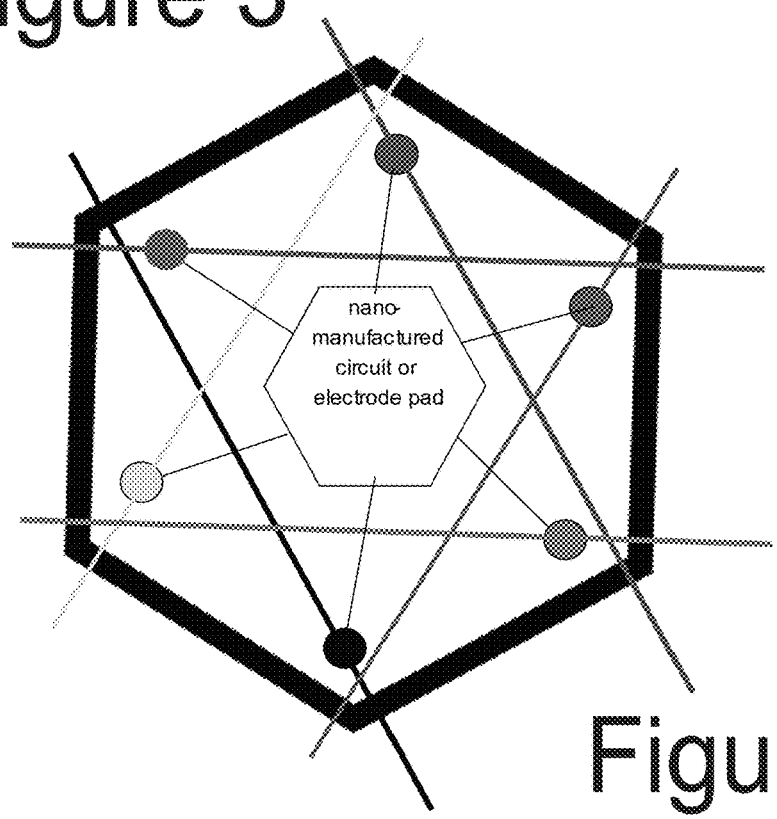
FIG. 4 shows an isolated view of one hexagonal connection element having six connection locations separately connectable with a corresponding conductor wire.

FIG. 3 shows an embodiment of the inventive functional fabric with six conductor wires integrated woven directly into fabric. FIG. 4 shows an isolated view of one hexagonal connection element having six connection locations separately connectable with a corresponding conductor wire. A fifth conductive thread may provide a first electrical apply connection and a sixth conductive thread a second electrical apply connection. The predetermined intervals and interlacing angles of the warp and weft of the plurality of interlaced threads may provide the first, second, third, fourth, fifth and sixth conductive threads so that the respective connection portions are each located at a corresponding vertices of a hexagonal connection area located at the regular intervals. A plurality of hexagonal connection areas may be located at the regular intervals on at least one of the top and the bottom face of the woven fabric.

Using a wiring protocol standard such as USB (4-wire bi-directional data with power) will allow fabric to include a multitude of individually addressable pixels. Packing in a hexagonal pattern provides for high pixel density. At the area of each pixel will be any of a variety of individual sensors, actuators or other USB compatible devices. Each pixel may be printed using nano-scale printing techniques. This will allow us to imprint individually addressable electrodes, sensors, communications devices, and so on throughout the matrix of fabric.

FIG. 4 shows an example hexagon "pixel" with the six electrical contact locations shown as Power (+) in red, Ground (−) in black, Data positive (+) in yellow, Data negative (−) in green, and AC (as used in TENS/EMS and/or other signal/power as required) shown in purple and blue pair.

Figure 9:
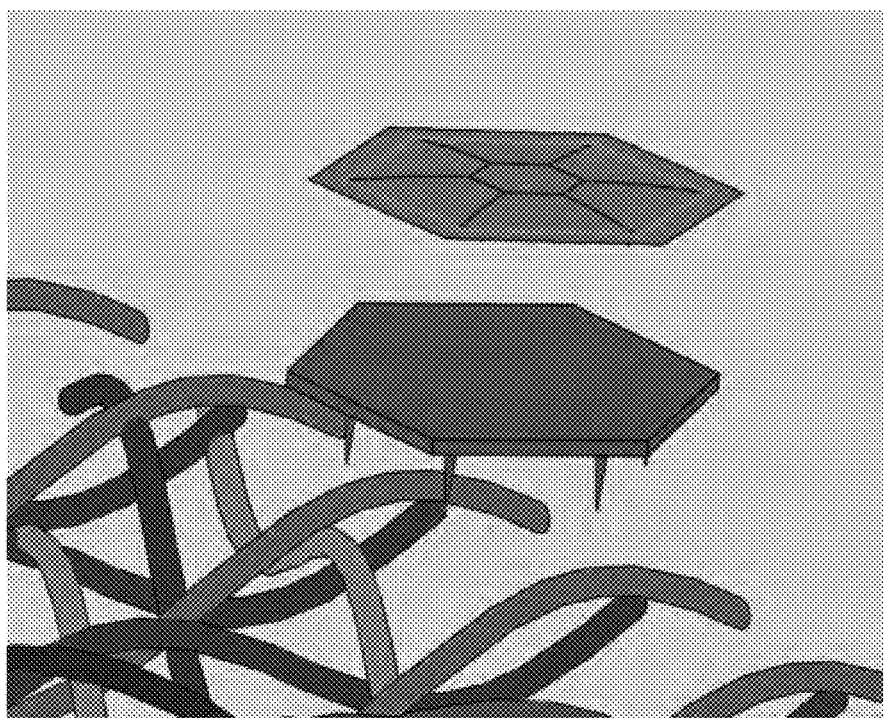
FIG. 9 is an exploded view showing a nano-circuit top layer above a hexagonal interface pad.

FIG. 9 is an exploded view showing a nano-circuit top layer above a hexagonal interface pad. A HEX interface pad shown in exploded view above edge of woven wire/fabric, and thin membrane nano-circuit top layer shown above HEX interface pad. The nano-circuit top layer can be made in a variety of configurations, allowing multiple individually addressable electrodes to populate the surface of the fabric. These HEX circuits can be made in multiple sizes, and can be "nested" with a single larger pad providing the interface to the fabric, and several smaller pads providing the multitude of functions (EEG, Sweat Chemistry, EKG, TENS/EMS, temperature, etc.)

Figure 10:
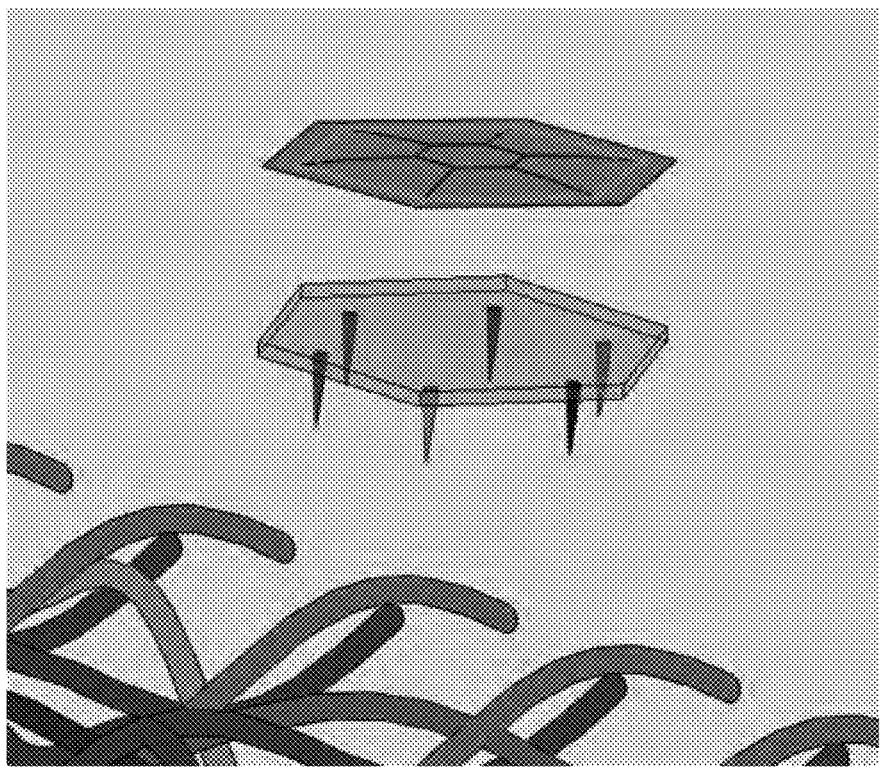
FIG. 10 is an alternative exploded view showing the nano-circuit top layer and hexagonal interface pad.

FIG. 10 is an alternative exploded view showing the nano-circuit top layer and hexagonal interface pad. Another view of the HEX interface pad and nano-circuit that will be adhered to top of HEX pad and will be provided electrical signal and communications interface to the garment through the electrical connections provided at the HEX interface pad.

A key point to recognize here is that each HEX interface pad will be provided with a standard 4-wire (USB or other standard) and a 2-wire AC (or other function) power and signal combination. As an alternative to wired communications, each interface pad may be enabled through direct wireless communications to pass data to and from the embedded electronics and a nearby wireless receiver/transmitter. This embodiment will facilitate nano and micro electronic Iot (Internet of Things) technologies that are presently under development. In this fashion, each HEX interface pad can be individually addressable (through serialized identification) and can control bi-directional signal to/from the pad surface/body. Functions of each pad will include a multitude of sensors (EEG, EKG, temperature, moisture, chemistry, etc.) and actuation (TENS/EMS, etc.).

At least one functional element may be connected to at least one of the connection portions of at least one of the conductive threads at at least one of the plurality of connection areas. Several pixel options will exist, including pixels with functional structures included in or composing all of circuitry specifically designed to accommodate chemical sensors (sweat chemistry), heat sensors, glucose sensors, EKG, EMG, EEG sensors, etc. etc., other pixels will perform as electrodes for TENS, EMS, etc., while other pixels can be made to perform as communications pixels (BLE, WAN, RFID, etc.), additional pixels could be navigation, movement and location components (GPS, IMU, magnetic sensor, etc.).

The functional fabric described herein can be applied, for example, to a haptic human/machine interface (HHMI) wearable electronic garment. The wearable electronic garment can be configured as a sleeve, legging, t-shirt, torso shirt, full body suit, glove, cap, wrap, or any other piece of clothing or garment that can be used to support and place electrodes, sensors, actuators, etc., on the body of a wearer and/or in face-to-face contract with the surface of the skin of the wearer.

Figure 11:
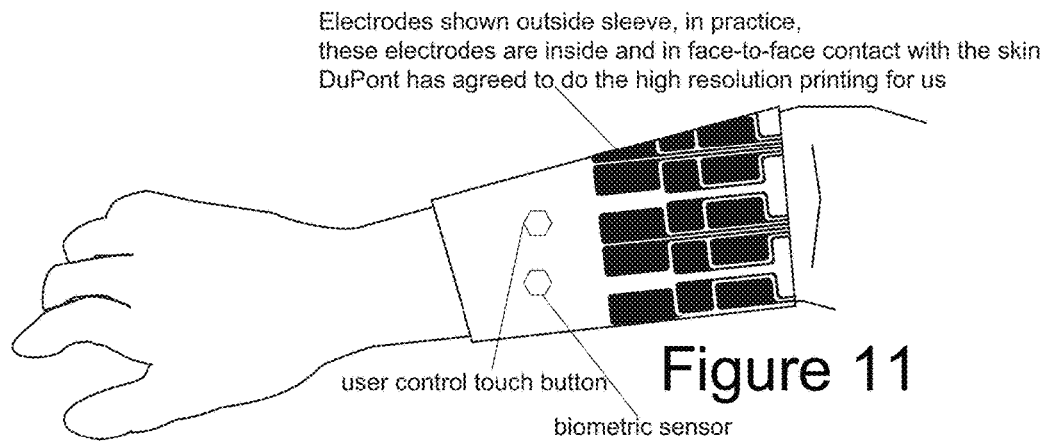
FIG. 11 illustrates an embodiment of an inventive wearable electronic sleeve with multiple individually addressable electrodes.
Figure 12:
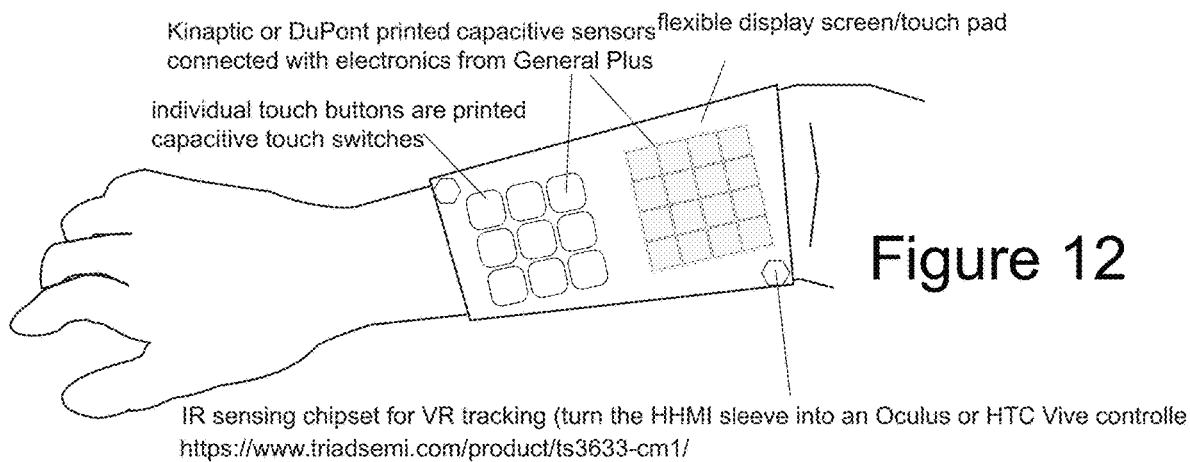
FIG. 12 illustrates an embodiment of the inventive wearable electronic sleeve with printed touch sensors and a flexible display.
Figure 13:
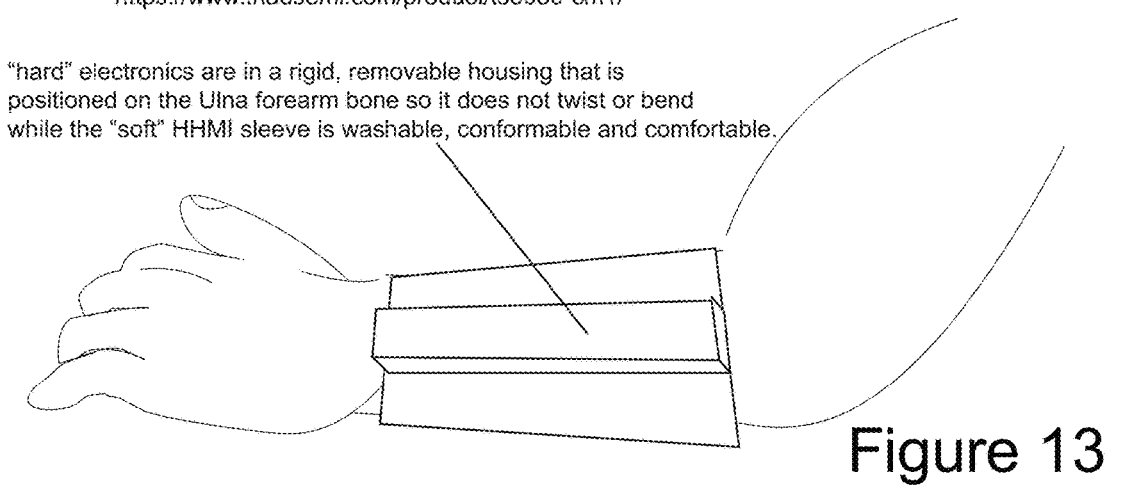
FIG. 13 illustrates an embodiment of the inventive wearable electronic sleeve with a hard electronic housing positioned on the ulna bone so the electronic does not twist or bend.
Figure 14:
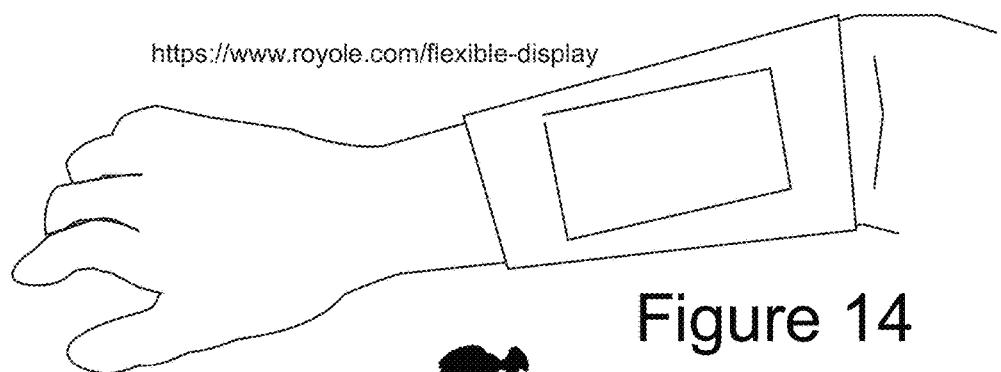
FIG. 14 illustrates an embodiment of the inventive wearable electronic sleeve with a flexible display.

As anon-limiting example configured as an HHMI wearable electronic garment that can utilize the inventive functional fabric described herein, and/or additional sensors, actuators, transducers, communication devices and other electronics using clothing as a support scaffold, FIG. 11 illustrates an embodiment of an inventive wearable electronic sleeve with multiple individually addressable electrodes. FIG. 12 illustrates an embodiment of the inventive wearable electronic sleeve with printed touch sensors and a flexible display. FIG. 13 illustrates an embodiment of the inventive wearable electronic sleeve with a hard electronic positioned on the ulna bone so the electronic does not twist or bend. FIG. 14 illustrates an embodiment of the inventive wearable electronic sleeve with a flexible display.

The inventive Haptic Human/Machine Interface (HHMI) can be configured as a wearable electronic platform with a large array of many individually addressable electrodes connected to a detection and application electronic unit. The architecture of the HHMI is uniquely adapted to mass production as a roll-to-roll manufactured printed electronic garment with embedded sensors and transducers. Just a few of the many applications for the HHMI include biometric sensing for health and fitness, stroke rehabilitation, tremor mitigation and pain relief.

As described herein, a signal multiplex circuit may be provided controlled by the microprocessor for routing the electrical signals from a signal generator (e.g., electronic muscle stimulator (EMS) or transcutaneous electrical nerve stimulator (TENS)) to the skin of the user through the electrode multiplex circuit; and to route electrical signals to a signal detector from the skin of the user through the electrode multiplex circuit. A memory may be provided controlled by the microprocessor for storing programming instructions and other data dependent on the biometric electrical signals; and a communication module for transmitting the stored data for analysis by a remote network device. The wearable electronic sleeve can include a housing comprised of an elastic fabric material, and the individually addressable electrodes that are dry electrodes may be formed by printing elastic conductive ink.

The same individually addressable electrode of the plurality of individually addressable electrodes can both detect the biometric electrical signals from the skin and apply the stimulation electrical signals to the skin. A microprocessor can control the electrode multiplex circuit to address the plurality of electrodes for sampling the biometric electrical signals at a sampling rate effective for the detection by the signal detector of the biometric signals as electromyographic signals originating from subcutaneous motor units indicative of muscle contractions from one or more muscles of the user.

The microprocessor can control the electrode multiplex circuit to address the plurality of electrodes for applying the stimulation electrical signals as application pulses at a pulse rate effective to cause involuntary contractions of the muscles of the user. The microprocessor can control the electrode multiplex circuit to address the plurality of individually addressable electrodes by at least one of sequentially and/or simultaneously routing both the biometric electrical signals from the skin of the user through more than one of the plurality of individually addressable electrodes to the signal detector and routing the stimulation electrical signals from the signal generator through more than one of the plurality of individually addressable electrode to the skin of the user. At least one of an inertial measurement unit, a sensor, a detector and a transducer may also be provided supported by the housing.

Figure 15:
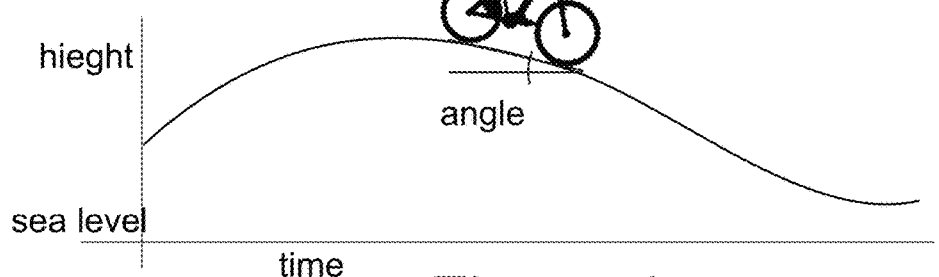
FIG. 15 illustrates a cycling use of an embodiment of the inventive wearable electronic sleeve.

FIG. 15 illustrates a cycling use of an embodiment of the inventive wearable electronic sleeve. A sports training system that uses the synchronized application of sensory cues is described in PCT Application PCT/US2016/026930 which is incorporated by reference herein. A wearable electronic, such as the wearable electronic sleeves described herein, or other suitable electronic device which may be mounted on the rider or on the bicycle, is used for data collection on a bicycle for use in sports training. The data collection may include, for example, biometric data including EMG, body position, heart rate, sweat chemistry, respiration, etc. The data may also include ambient and environmental data including temperature, humidity, daylight, wind speed, air chemistry, etc.

A microprocessor controls the reception of data from sources such as a GPS, microphone, camera, gyroscopes, accelerometers, speedometers, etc. This data is logged by a data logger and stored in a memory. As described herein, synchronized application of sensory cues dependent on the data collection can then be applied to the user during a training session. During the training session, the logged data is retrieved from memory and used by the microprocessor to determine a plurality of first sensory cues. The sensory cues are generated by the microprocessor and made available for perception by the user, for example, the sensory cues can be a spherical point of view video that is viewable from all angles using head tracking AR or VR headset. The plurality of first sensory cues are time-sequentially generated and effective for stimulating at least one sense of the user, such as vision. A plurality of haptic sensory cues is generated capable of being perceived by the user. The haptic sensory cues may be received by the user dependent on computer-controlled time-sequentially generated electrical signals. For example, the haptic sensory cues can be applied using the HHMI and create the sensation of wind rushing over the arms of the user where the wind speed is dependent on the virtual cycling speed. A fan synchronized to the virtual movement of the cyclist while engaged in the actual riding of a stationary bicycle can also be used to create the sensation of air movement that correlates to the virtual speed of the cyclist (and/or that correlates to the rotational speed of the cyclist's stationary bicycle tires as if the bicycle was moving and not stationary).

Additionally, or alternatively, the haptic sensory cues can be a varying resistance force applied to resist the pedaling motion of the user as if the user is cycling up and down the hills of the course. These electrical signals invoke a perception by the user related to the sense of touch and movement. The haptic sensory cues are generated in synchronization dependent on the time-sequentially generated plurality of first sensory cues. For example, as the speed of the bicycle goes faster, as indicated to the user by the scene on the VR headset showing the virtual view of cycling up and down the hills of the course, the apparent wind speed on the arms of the user also increases by applying an appropriate computer controlled haptic signal.

A collection of data sampled along an actual route (or created by a computer simulation) is used to create a realistic riding experience for the stationary cyclist wearing a VR or AR headset or viewing on a flat screen or mobile device. The collection of data sampled along the route may include the bicycle at an angle and height relative to the horizon and sea level. The collected data is used by the microprocessor to calculate a resistance value to be applied by a resistance controller to a training system of a stationary bicycle. Friction brakes, electrorheological fluid brakes, magnetic brakes, and other electronically variable resistance braking mechanisms can be used to create the resistance applied in synchronicity with the haptic, visual and other sensory cues. The resistance may be, for example, calculated dependent on data such as the angle of the bicycle relative to horizontal (e.g., the steepness of the hill when the actual cycle route is taken), user weight, GPS data, speed, etc. Some of the data can be directly collected during the ride along the route or calculated/approximated by the microprocessor. As an example, a cyclist can train on a stationary bicycle but experience the legs of the Tour de France as a virtual experience.

As an Accelerated Learning training system, the conditions (such as, grade of the terrain, wind conditions, etc.) from a real-world bicycle course (say, a leg of the Tour de France) are obtained, stored, and/or otherwise generated, and used to automatically control the pitch of the bicycle, the resistance of the rear wheel to the user's leg power, and even the breeze felt by the rider—all can calculated from the real-world course conditions and/or computer created. In the Tour de France example, when riding "downhill" the user will see the country side of France, the roadway, the sights and sounds of the crowd and other riders, and even feel the force of the wind pick up as the user picks up virtual speed on the downhill run. A virtual race can be created where avatars of other riders throughout the world are in the user's virtual reality experience and user is in theirs.

Over time, the rider may become more optimally trained in all aspects of the course, from when to change gears, how hard to push up hills, how fast to safely go down hills—even when to hydrate and fuel up the body to optimize his performance on the real-world course.

An ultra-deep immersion in a VR scenario, including involuntary muscle contractions from the HHMI wearable electronic that are synced to VR audio and visual cues, is an effective means for building up rapid muscle memory and pattern recognition (the basis of all physical learning). The ultra-deep immersion may include the repurposing of 360-degree or other content, for example, from Google earth. As an example, based on GPS data the terrain of many potential bike routes can be virtually re-created so that the VR content can be matched up with the pitch of the cycle to create the realistic hills and terrains. This would allow, for example, a weekend warrior to train on the virtual course of an upcoming local or distant triathlon. Popular locations might get better video capture resolution, so the user can take a virtual bike tour, for example, of the San Francisco streets.

The ultra-deep immersion described above can be used for a variety of applications described herein for gaming, accelerated learning, stroke rehabilitation, bicycle training, etc., and may be further adapted for other sports, military and musical training applications. A non-limiting exemplary embodiment of the inventive method includes detecting non-biometric data detecting at least one of a position of a bicycle relative to a fixed geographic location, selected gears, and ambient and environmental data. Biometric data is detected detecting at least one biometric signal from a rider of the bicycle, the at least one biometric signal including at least on of EMG, body position, heart rate, sweat chemistry, body temperature, and respiration. The detected non-biometric data and the detected biometric data is recorded. Computer-controlled first sensory cues are generated dependent on at least one of the recorded non-biometric data and biometric data. The first sensory cues are applied to a user. A plurality of visual sensory cues is generated capable of being displayed to the user on a video display device. The visual sensory cues are effective for stimulating a visual processing area of the brain of the user synchronized with the first sensory cues. The visual processing area is stimulated with a visual sensory cue in synchronization with the first sensory cue stimulating the first processing area. The synchronized stimulation of the first processing area and the visual processing area is effective for building up muscle memory to strengthen the user's brain and nervous functions that control the change in the position of the at least one body part.

The plurality of first sensory cues can comprise at least an electrical signal applied to muscles or nerves of the user to induce involuntary muscle contraction to cause movement and change a position of at least one body part of the user. The electrical signal can be applied as the first sensory cues to the user to cause the involuntary muscle contraction to cause movement and change the position of the at least one body part of the user in response to the electrical signal applied to the user. The visual sensory cues provide a virtual visual indication to the user of the change in position of the at least one body part so that the change in position of the at least one body part is virtually visually indicated in synchronization with the change in the position of the at least one body part. The at least one body part is at least one leg of the user. The visual sensory cue may include a visual scene related to riding of the bicycle. The applied electrical signal can cause the induced movement of the at least one leg synchronized with the visual sensory cue for building up muscle memory to strengthen the user's brain and nervous functions that control the change in the position of the at least one leg.

A second plurality of sensory cues can be generated capable of being perceived by the user. Each second sensory cue of the plurality of sensory cues may be dependent on at least one of the recorded non-biometric data and the recorded biometric data. The second sensory cues can be effective for stimulating at least a second processing area of the brain of the user. The second sensory cues can be synchronized with the first sensory cues so that the second processing area is stimulated with a second sensory cue in synchronization with a first sensory cue stimulating the first processing area. The synchronized stimulation of the first processing area, the visual processing area and the second processing area is effective for building up muscle memory to strengthen the user's brain and nervous functions. The first processing area can be at least one of a touch and a movement processing area of the brain. The second plurality of sensory cues may comprise auditory sensory cues, and the second sensory processing area can be an auditory processing area.

The video display device may comprise at least one an augmented or virtual reality headset, a computer monitor, a television, a smart phone display or a personal information device display.

The first sensory cues can be applied to the user using a wearable electronic comprising a woven fabric formed from a plurality of interlaced threads, the plurality of interlaced threads comprising a plurality of warp threads interlaced with a plurality of weft threads, the woven fabric having a top face and a bottom face, a plurality of conductive threads included among the plurality of interlaced threads at predetermined intervals and interlacing angles to provide a pattern of connection locations, wherein the connection locations are located at regular intervals on at least one of the top face and the bottom face of the woven fabric, and electrodes disposable in electrical contact with skin of the user, wherein the plurality of conductive threads carrying the electrical signal to electrodes for applying the electrical signal through the skin of the user to at least one of muscles and nerves of the user to cause the involuntary movement.

The biometric data can be detected from the rider of the bicycle using a wearable electronic comprising a woven fabric formed from a plurality of interlaced threads, the plurality of interlaced threads comprising a plurality of warp threads interlaced with a plurality of weft threads, the woven fabric having a top face and a bottom face, a plurality of conductive threads included among the plurality of interlaced threads at predetermined intervals and interlacing angles to provide a pattern of connection locations, wherein the connection locations are located at regular intervals on at least one of the top face and the bottom face of the woven fabric, and electrodes disposable in electrical contact with skin of the rider, wherein the plurality of conductive threads carrying the electrical signal from electrodes for detecting the biometric data from the skin of the rider.

Figure 16:
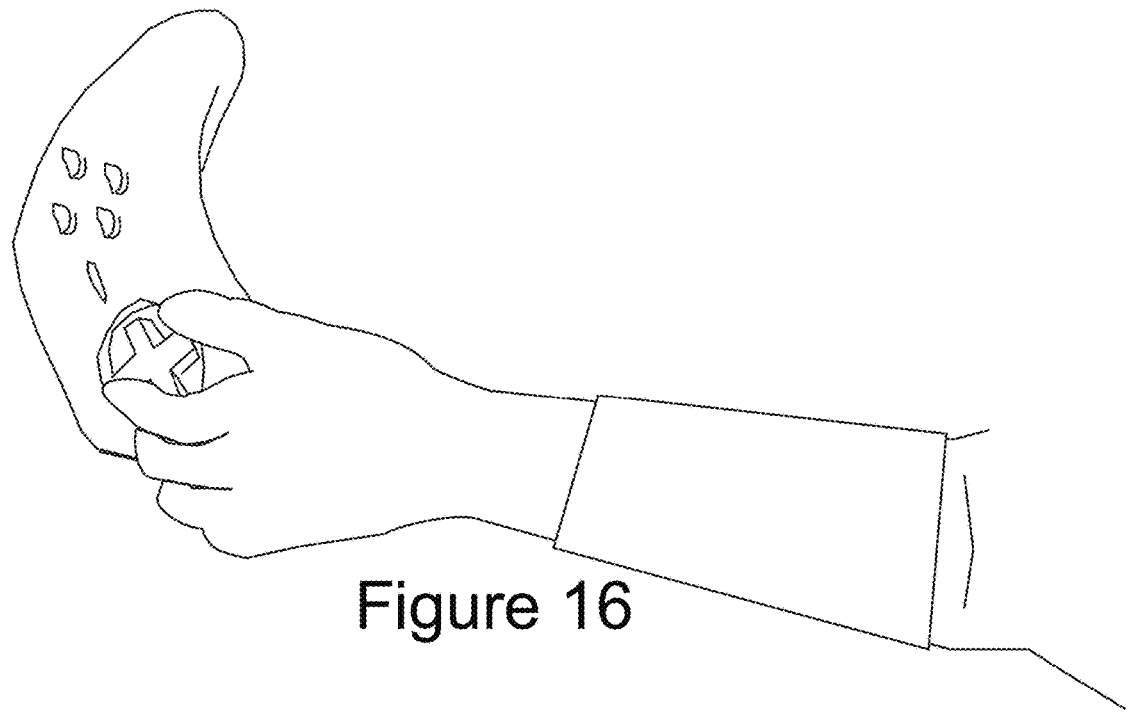
FIG. 16 illustrates an embodiment of the inventive wearable electronic sleeve used in conjunction with a gaming controller.
Figure 17:
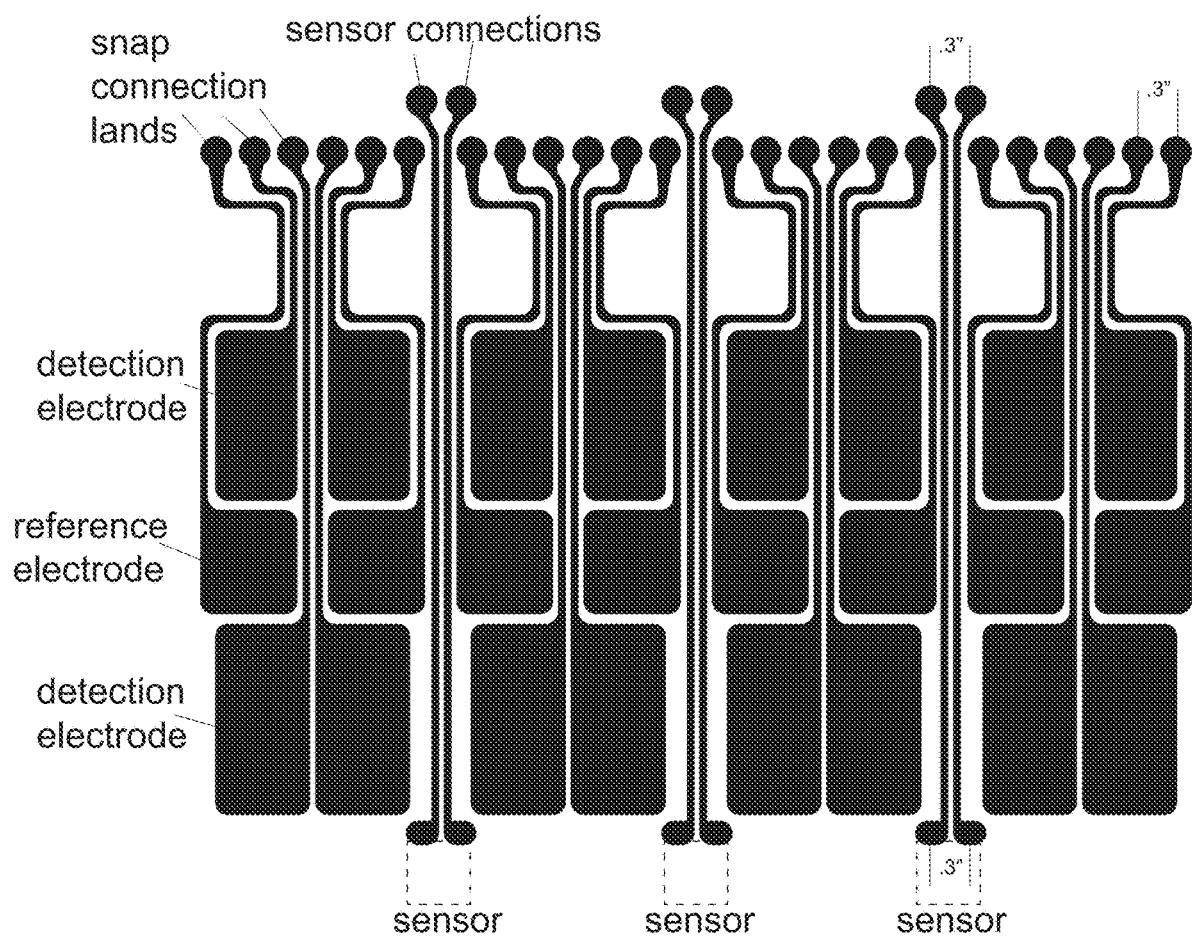
FIG. 17 shows a pattern of individually addressable electrodes.
Figure 18:
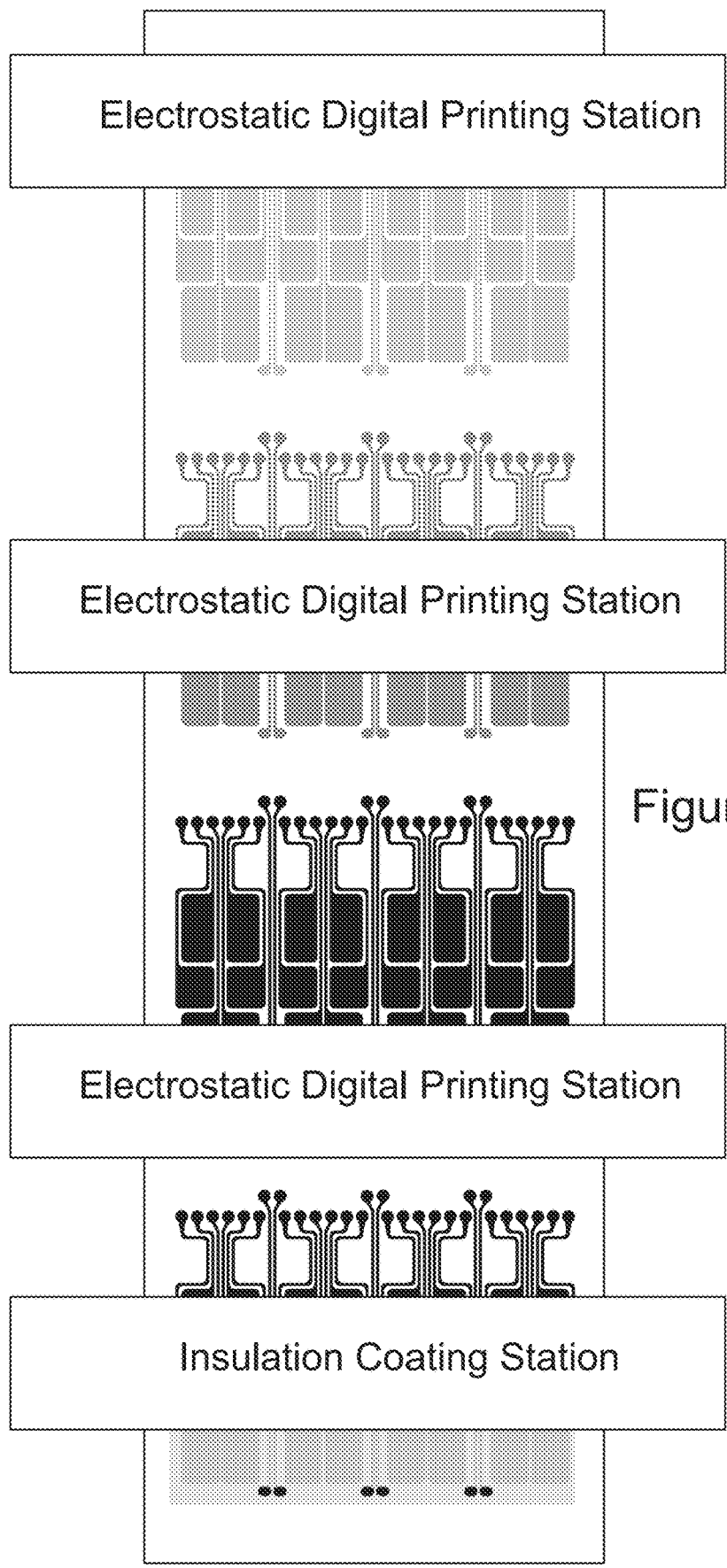
FIG. 18 shows a digital printing method and apparatus for printing the individually addressable electrodes on a wearable electronic substrate material.

FIG. 16 illustrates an embodiment of the inventive wearable electronic sleeve used in conjunction with a gaming controller. FIG. 17 shows a pattern of individually addressable electrodes. FIG. 18 shows a digital printing method and apparatus for printing the individually addressable electrodes on a wearable electronic substrate material.

The inventive HHMI can be configured as a sleeve and applied as a retrofit modification or OEM device in signal communication with a gaming controller. The HHMI may communicate over a wireless or wired connection with a console or hand controller, such as an X-box, Playstation, Wii, Nintendo, or other gaming platform. The typical gaming controller includes a vibrating element (sometimes called a "rumble pack"). Much of the gaming software makes use of the rumble pack to provide haptic feedback, for example, to provide a somatic vibrating sensation when a grenade explodes, or a rocket ship takes off, or a car engine revs. In accordance with this aspect of the invention, the HHMI can make use of the control of the rumble pack during game play of an existing game or using code written specifically for the HHMI so that a haptic cue is applied to the user. A microprocessor may be used to generate a specific haptic cue corresponding to the software code making up the game.

Non-limiting, exemplary embodiments show the HHMI as a wearable electronic garment having a grid of individually addressable dry electrodes that detects muscle and nerve activity, analyzes the detected signal, and generates a corresponding activation signal that is applied via the same electrode grid to create movement and touch sensations.

In accordance with an exemplary embodiment, a wearable electronics device architecture and fabrication method are provided for generating an HHMI wearable electronic that includes a high-speed multiplexing electronic circuit connecting a large array of many individually addressable electrodes to small number of detection and application electronic units. The architecture of the HHMI is adapted to mass production as a roll-to-roll manufactured printed electronic garment with embedded sensors and transducers.

An exemplary embodiment of the HHMI utilize existing stretch fabrics (such as Lycra and Spandex), printing techniques (including screen printing, stamping and inject printing), and mature roll-to-roll lamination processing technology that has previously been used, for example, in the sign making industry. In accordance with an exemplary manufacturing process, these previously known manufacturing techniques are modified to create a new high yield batch and roll-to-roll manufacturing process for fabricating wearable electronics products.

The exemplary embodiments of the HHMI can be used for example, for accelerated learning, imparting muscle memory and pattern recognition through the simultaneous stimulation of the auditory, vision and haptic (touch and motion) processing areas of the brain. The exemplary embodiments of the HHMI can be configured as wearable electronic products that use screen printed elastic, conductive electrodes and a high speed, multiplexing circuit that significantly reduces costs, failure modes, bulk, battery consumption and weight of the wearable electronic.

The HHMI construction can be used to make a SmartShirt™. In accordance with this aspect of the invention, the HHMI includes wearable electronic product architecture, manufacturing methods, for capturing high fidelity biometric data from the human body. The HHMI advantages include lower cost, easier to use form factor, wearable products with wide range of sensors and embedded AI software. The HHMI has unique bi-directional detect/analyze/apply capability that enables proactive responses such as active transdermal drug delivery and transcutaneous electrical nerve stimulation automatically applied or remotely triggered by a monitoring physician. Biometric data can captured and transmitted continuously or during selected times with data access provided directly to careprovider, enabling early diagnosis and ongoing monitoring.

This data detection is direct from the human body and can also be provided for Blockchain and AI database collection, access and analysis.

The HHMI provides secure and accurate detection and transmission of biometric data. The biometric data that can be collected includes but is not limited to electrical signals (EMG, EKG, etc), sweat chemistry (almost every chemical component in the blood can be detected through the sweat), physical attributes (body temperature, location) and ambient conditions (air temperature, air quality, etc.). The HHMI wearable electronic garments provide bi-directional capabilities to detect/analyze/apply signals to/from the human body. The HHMI distributes a large array of individually addressable electrodes and sensors, enabling a single sensor or signal generator to service many electrodes, with multiple small electrodes forming physiology matching patterns. The Haptic/Human Machine Interface (HHMI) technology is fully bi-directional, utilizes nano-scale printed electronic sensors, providing high-resolution data in a rugged, machine washable garment.

Figure 19:
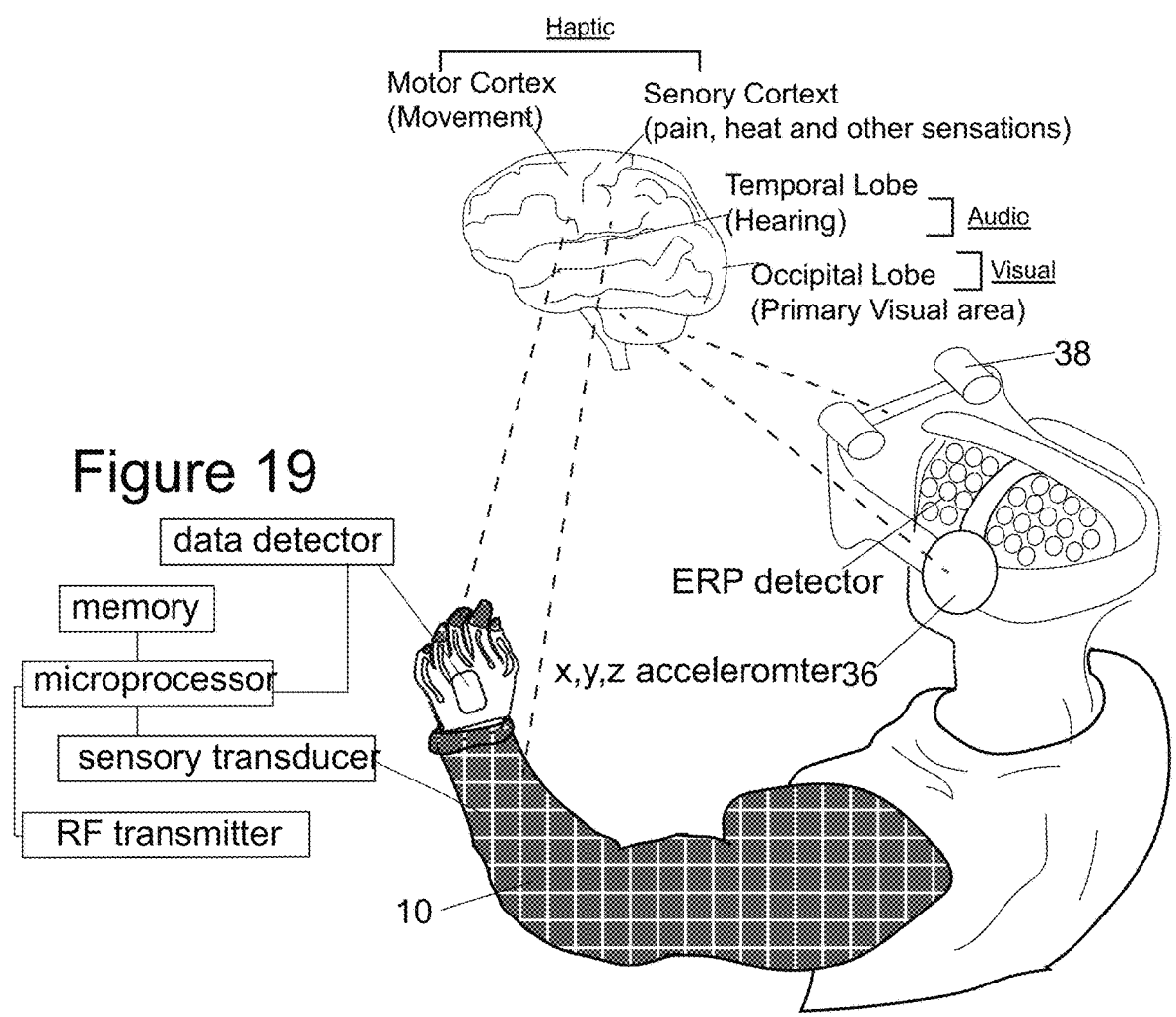
FIG. 19 illustrates the premise for Accelerated Learning through the simultaneous synchronized application of computer-controlled sensory cues to stimulate multiple processing areas of the brain.

FIG. 19 illustrates the premise for Accelerated Learning through the simultaneous synchronized application of computer-controlled sensory cues to stimulate multiple processing areas of the brain, used for example for VR Stroke Rehabilitation. An application of focus for the HHMI is the use for stroke rehabilitation. Stroke is the second leading cause of death and a leading cause of long-term disability. Most of the victims of stroke end up immediately experiencing persistent paralysis of the upper limbs. Researchers using functional magnetic resonance imaging (F-MRI) have demonstrated that VR training systems can be used to create brain rewiring (i.e., cortical reorganization) in stroke patients. Although the human brain, and the brains of many animals, have now been shown to have a high degree of neuroplasticity, there needs to be an external prompt to effectively rewire a damaged brain. It has been shown that simple task repetition is not sufficient to induce neural plasticity and learning. To induce brain rewiring there needs to be an impetus that triggers the brain's inherent capability to form new neuronal pathways. The is a need for creating neuronal pathways prompting for new brain connections using a motivating and enjoyable VR scene, along with computer-controlled involuntary muscles contractions.

In accordance with an embodiment, an accelerated learning system provides rehabilitation to a stroke victim. The various portions of the brain related to the processing of sound, touch and vision can be controllably and simultaneously stimulated so that a weakened brain's processing area can be strengthen or rewired through the support of stronger, intact, brain sensory stimulation processing areas. For example, a stroke victim with damage to the right-side motor cortex may have a loss of function in the motor control of the fingers of the left hand. Using the HHMI, haptic sensory cues and involuntary muscle contractions are applied to the fingers of the left hand. These touch and movement sensory cues stimulate the damaged portions of the brain, while corresponding, synchronized virtual reality visual and audio cues reinforce the re-learning or rewiring of the damaged portions of the brain.

The human body can be considered a finely tuned machine, with electrical systems (i.e., nervous system) that communicate control signals from a central processing unit (i.e., the brain). When the lines of communication are broken or the ability to generate electrical signals are damaged, the finely tuned human machine becomes dysfunctional. Usually, there is no immediate damage to the limbs or other body parts caused by a stroke, the structure for movement remains intact, but the patient is paralyzed because the damaged brain fails to provide the appropriate control signals.

The inventive HHMI technology can be used for rehabilitating a stroke-damaged brain to prevent and reverse paralysis, bring back speech and other lost cognitive functions, and repair the damage caused by the interruption of the neuronal pathways resulting from stroke. The HHMI wearable electronic product architecture, manufacturing methods, and electrical signal application and detection techniques apply haptic sensory cues and create computer-controlled involuntary muscle contractions through skin surface applied dry electrodes. These haptic cues and involuntary muscle contractions are synchronized with virtual reality audible and visual cues to simultaneously stimulate multiple processing areas of the brain. Using the brain's inherent neuroplasticity, these synchronously applied sensory cues along with the physical involuntary movement of an affected limb result in the rapid build-up of muscle memory and pattern recognition to effectively rewire the stroke-damaged brain.

Most stroke rehabilitation is done through expensive physical therapy by a highly trained professional at a clinic. Intervention in the form of drugs and surgery is utilized, of course, to first stabilize the body and prevent further brain damage. The HHMI allows the brain's inherent ability to reform neuronal connections by applying the kick-start of haptic sensory cues and computer-controlled involuntary muscle contractions, in conjunction with a pleasant and calming virtual reality audio and visual scene. The ultra-deep VR immersion puts the patient into a new physical learning mode that creates the rapid build-up of muscle memory and pattern recognition. This effectively reroutes the neuronal pathways around the stroke-damaged areas of the brain, creating new connections that reverse or mitigate affect limb paralysis and remediating other stroke-related issues including range of motion, depression, tremor and pain. Importantly, this therapy can be applied while still in the hospital immediately after the body has been stabilized. There is strong evidence that early therapy is an effective way to get the brain to rewire around damaged areas and in the case of paralysis, prevent the rapid loss of muscle tone and onset of muscle atrophy.

In accordance with an embodiment, the naturally occurring electrical systems of the human body are utilized to overcome and mitigate the dysfunction and challenges caused by a stroke damaged brain and use the brain's inherent neuroplasticity to rewire the damaged brain and restore a high degree of functional life skills and cognitive capability back to the stroke victim.

Stroke researchers have long known that effective task-oriented training programs should be challenging enough to require new learning, progressively and automatically advancing according to each patient's individual rehabilitation progress, and stimulating enough to really engage the patient in a creative, realistic and demanding effort.

VR Stroke Rehabilitation offers numerous advantages over other traditional physical rehabilitation. VR immersion turns boring, repetitive tasks into interesting, motivational, challenging virtual activities. Also, the difficulty of virtual tasks can be easily and automatically tailored to the patient's ability and rehabilitation progress. VR is very well suited to provide skill training with immediate and accurate performance feedback through visual and auditory rewards, increasing a patient's motivation to practice the virtual tasks that lead to regaining real-world life skills.

The inventive VR Stroke Rehabilitation system creates rapid rerouting or rewiring of the various communication signals between processing areas of the brain. For example, if the portions of the brain related to auditory processing are damaged, visual and haptic sensory cues, along with the audio cues, are computer generated to stimulate the various processing areas of the brain and reinforce newly learned auditory responses as the brain rewires those specific portions related to auditory processing.

A basic premise is to use trans-dermally applied electrical signals to provide haptic sensations and involuntary muscle contractions. These touch and movement cues are applied simultaneously with virtual reality video and audio cues from a VR headset. The simultaneously applied sensory cues stimulate the different processing areas of the brain and result in rapid muscle memory and pattern recognition. The basis of all physical skills learning.

Although stroke rehabilitation can significantly help in the recovery of upper-limb function, the effectiveness of conventional stroke therapy is generally less effective in the upper limbs than in the lower limbs. Even with successful therapeutic intervention, most stroke survivors continue to experience functional limitations in their upper extremities many months after a stroke.

The inventive VR Stroke Rehabilitation system uses ultra-deep VR immersion, along with the computer controlled involuntary muscle contractions and haptic sensations as an effective non-drug, non-surgical modality for improved stroke rehabilitation that can be used as an alternative or in conjunction with more traditional physical therapy. As an example-use of the inventive VR Stroke Rehabilitation system, it is well known that even after a stroke victim regains the use of their arm, there is often a persistent limitation of the pinch movements that allow the patient to grasp an object. The pinch movements represent an important upper-extremity motor skill. Even after successful rehabilitation of the arm, it is often the case that impaired pinch substantially affects a persons' dexterity after a stroke.

The inventive VR Stroke Rehabilitation system can be applied as a rehabilitation device to induce movement in the individual fingers on a hand. That is, the muscles that control movement of each finger can be separately targeted by electrodes and/or other transducers including vibrators and buzzers.

An example inventive VR Stroke Rehabilitation system methodology is the teaching of a musical instrument, such as a keyboard. Multiple sensory cues are simultaneously received by the stroke victim's brain. Audio (musical tones), visual (displayed hand position on a keyboard) and haptic (electrical stimulation and/or vibration applied to individual fingers corresponding to notes being played) are used to "teach" a patient how to play a simple song on a piano keyboard. Providing the simultaneously applied multiple sensory cues strengthens the patient's brain and nervous functions that control hand movement.

The inventive HHMI wearable electronic enables the application of electronic stimuli for triggering somatic and kinesthetic events in human-computer interfaces. As with other uses for the HHMI, some of which are described herein and/or in documents incorporated by reference herein, the inventive VR Stroke Rehabilitation system makes use of the somatic and kinesthetic systems of the body to enable the sensations that relate to force and touch. The somatic system perceives sensations from the skin surface and from below the skin surface, and the kinesthetic system perceives movement related sensations in the joints and muscles. In general, these sensations are called haptic feedback and inform the human brain on geometry, texture, temperature. weight and inertia. Skin and muscle sensations are received by several receptors: thermoreceptors, nocireceptors, mechanoreceptors including proprioceptors and chemical receptors. In theory, every kind of nerve or nerve ending, or receptor can be triggered using the HHMI wearable electronics technology. These stimuli differ in pulse length, frequency, amplitude and triggering mode. For stroke rehabilitation, the ability to deeply immerse the patient in the touch, movement, sight and sounds of a virtual scene will quickly build up lost muscle memory and pattern recognition, bring resiliency back to the damaged brain and fortify against secondary stroke damage (the number one killer from stroke occurs when a victim's damaged brain suffers a second stroke).

The inventive HHMI wearable electronics applies computer controlled electrical signals with signal characteristics effective to stimulate one or more of the tactile receptors found in the skin. For example, neuromuscular electrical stimulation is applied as a low frequency, relatively high intensity pulse. The pulse, which may be biphasic, triggers the alpha motor nerves that cause muscle movement. The higher the intensity of the electrical stimulus, the more muscle fibers will be excited, resulting in a stronger contraction. The contraction can have different speeds and duration of the contraction dependent on the characteristics of the applied electrical signal. The characteristics of the applied electrical signal can be controlled to cause isometric and/or isotonic muscle contraction, where an isometric muscle contraction leads to a tension in a muscle, without changing the length of the muscle, and isotonic muscle contraction, results in a shortening of the muscle.

In accordance with the inventive haptic interface, a computer controls the characteristics of electrical signals applied to, for example, the motor neurons of the patient's nervous system to cause a desired sensation and/or muscle movement. Exciting the motor neurons via the body's nervous system produces substantially the same result as when the neurons are excited through the computer controlled electrical stimulation. The signal characteristics are controlled to selectively stimulate the receptors that have, for example, different receptive fields (1-1000 mm2) and frequency ranges (0.4-800 Hz). Touch sensation are possible along with involuntary muscle contractions to further deepen the VR immersion and increase the effectiveness of the VR Stroke Rehabilitation therapy. For example, broad receptive-field receptors like the Pacinian corpuscle produce vibration tickle sensations. Small field receptors such as the Merkel's cells, produce pressure sensations.

The inventive HHMI wearable electronic platform has a wide range of medical, military, educational, entertainment and sports training applications. The HHMI enables the next generation of stroke rehabilitation by combining wearable computing with an immersive haptic interface and augmented/virtual reality. The HHMI is configured in combination with virtual reality vision and auditory systems to create an easy to wear, washable, comfortable, wearable electronic for stroke rehabilitation. The HHMI wearable electronic can apply a variety of haptic sensation and muscle and nerve stimulation, and can be used to detect EMG and other electrical, chemical, and biometric signals, as well as detecting proximity, temperature, color, and other environmental signals.

The HHMI provides transcutaneous electrical activity detection of the muscles and nerves involved in the intended control movements of the stroke victim. In response to the detected control movements, involuntary muscle contractions are generated to complete an intended movement, such as moving the hand from plate to mouth, allowing a stroke victim to regain the life skill of being able to feed himself. The sense of proprioception is gained primarily from input from sensory nerve terminals in muscles combined with input from the body's vestibular apparatus. This is achieved through the virtual reality experience and the haptic and movement cues that re-teach the stroke victim the lost life skill. The HHMI stimulates the nerves and muscles to produce a haptic sensory experience that is directly related to the desired life skills task.

As a simplified, basic example, the HHMI signal detection and application components include an EMG sensor located at the belly of the extensor digitorum and a TENS signal-applying electrode is located at either end of the muscle. A movement detecting accelerometer is located on the back of the hand. In the actual HHMI system, the sensors and electrodes are more numerous, with an optimal size, number, type and shape of the electrodes dependent on the particular application.

The HHMI is capable of detecting the data from EMG electrodes, accelerometers and inertia sensors fixed to the body appendages. For signal generation and application, the HHMI multiplex electronic circuit works with the HHMI microprocessor to create a selectable array of electrodes. To keep costs and complexity low, the detection and application of electrical signals from/to the body is achieved using a unique multiplex circuit with many electrodes allowing for a high resolution and large skin surface area coverage. For the application of the generated signal to the body, the generated signal is directed through the multiplex circuitry so that the signal will be selectively applied to the precisely targeted muscles and nerves. This high-speed switching multiplex circuit enables very high sample and signal application rates allowing a large number of smaller sized individually addressable electrodes to selectively detect and apply signals, increasing the detection resolution and the finesse of stimulated sensations and involuntary movement.

Augmented and virtual reality headsets, and binaural headphones, are paired with the HHMI to enable varying degrees of mediated reality immersion. The HHMI is combined with recently available Augmented and Virtual Reality systems to enable computer-controlled sensory cues (haptic, audio, and visual) to be applied to rewire the brain through the simultaneous application of synchronized sensory cues. For example, the HHMI can be paired with an Oculus Rift, HTC Vive, or other virtual reality headset or with the augmented reality headset, such as the Metavision AR headset.

During a stroke rehabilitation session, the HHMI takes advantage of the brain's neuroplasticity to build muscle and pattern memories in a form of accelerated learning system to re-teach the stroke victim lost life skills. The HHMI is used to reinforce the association of motor actions with specific sound and visual patterns corresponding to the life skill, while receiving continuous multi-sensory feedback. The connections between auditory and motor regions (e.g., arcuate fasciculus of the brain's frontal lobe) are strengthened while multimodal integration regions (e.g., around the intraparietal sulcus of the brain's parietal lobe) are activated. During the rehabilitation session, the HHMI creates a virtual cognitive experience composed of simultaneously applied sensory cues that stimulate the touch, hearing and visual processing areas of the patient's brain. The visual sensory cues of the experience will be seen by the subject through the VR/AR headset. The audio sensory cues will be heard through high quality binaural headphones. The touch sensory cues are applied through the HHMI wearable electronic garment.

The uses for the HHMI go beyond stroke rehabilitation. The HHMI opens new avenues in human/machine interaction and control, that also impacts areas of accelerated learning, physical training and rehabilitation. The ability to identify muscle groups at a sufficient level of definition, and the ability to apply electrical signals at a similar level, enables an HHMI system in which previously-known actions and muscle movements could be developed for improved physical training and correction of physical motion. Using the HHMI wearable electronics platform, memory associated with nearly all kinds of human activities can be more quickly developed to learn, for example, a musical instrument or sport technique.

Figure 20:
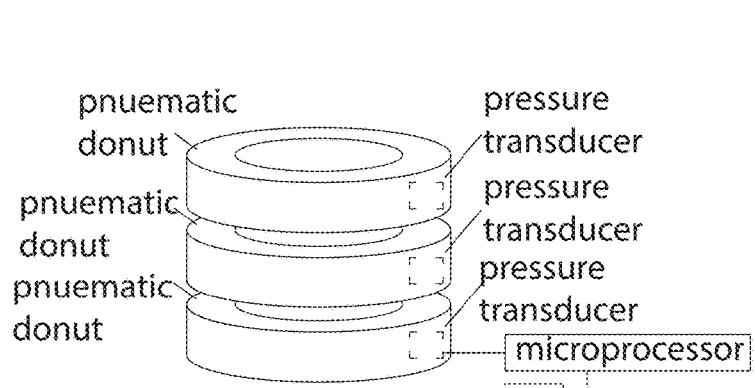
FIG. 20 shows a stack of pneumatic pressure transducers of an inventive virtual reality strike pole.
Figure 21:
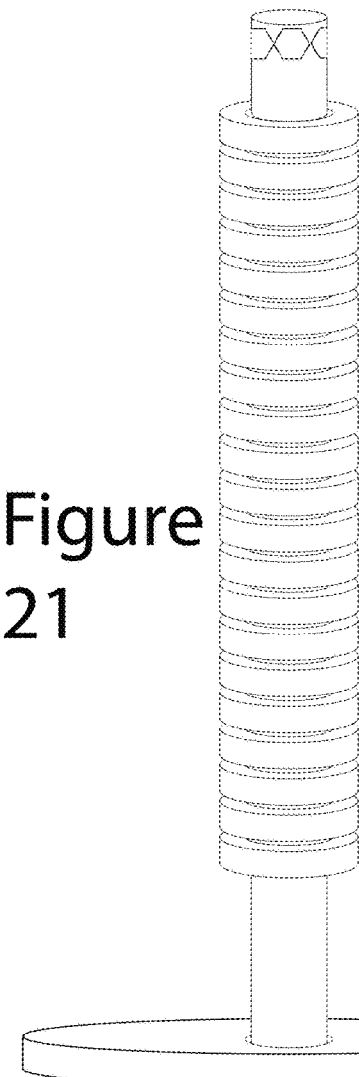
FIG. 21 shows the inventive virtual reality strike pole having a stack of pneumatic pressure transducers and a position detecting system.
Figure 22:
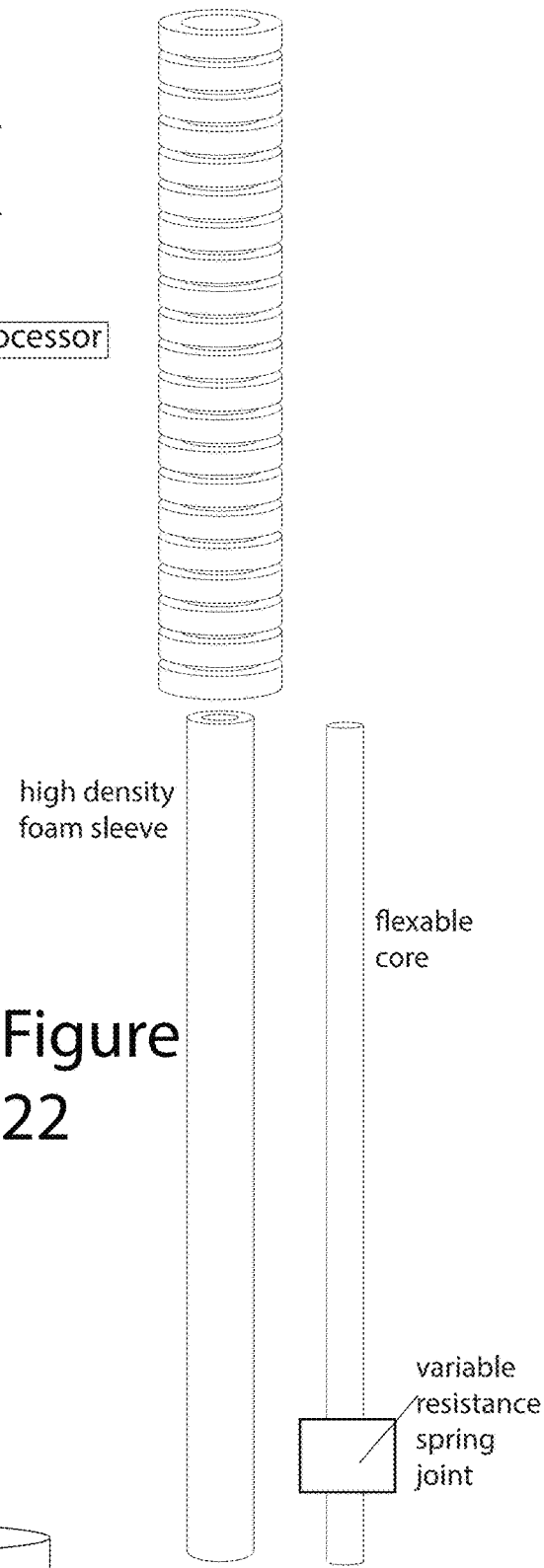
FIG. 22 shows an exploded view of the inventive virtual reality strike pole.
Figures 23, 24:
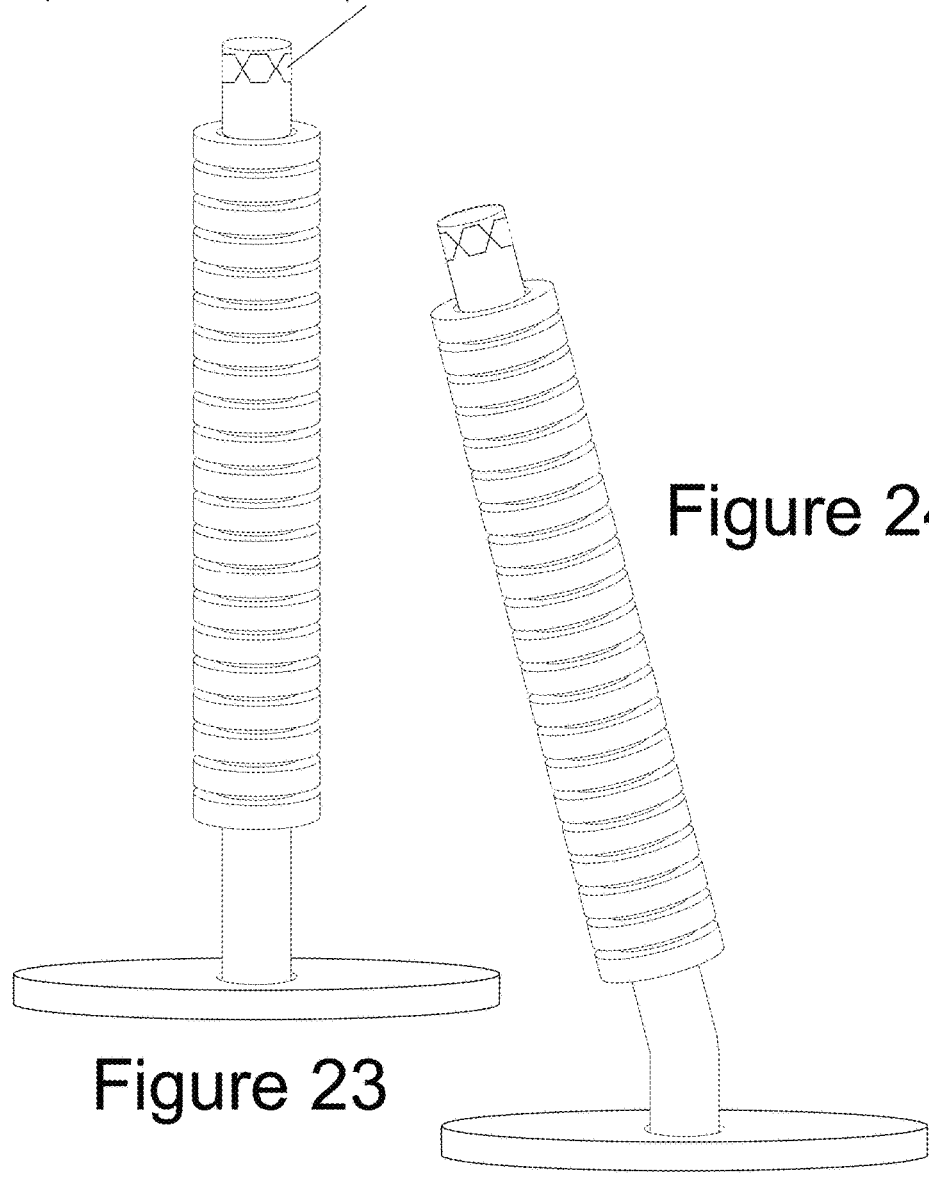
FIG. 23 shows the inventive virtual reality strike pole at a resting position.
FIG. 24 shows the inventive virtual reality strike pole at an active position.
Figure 25:
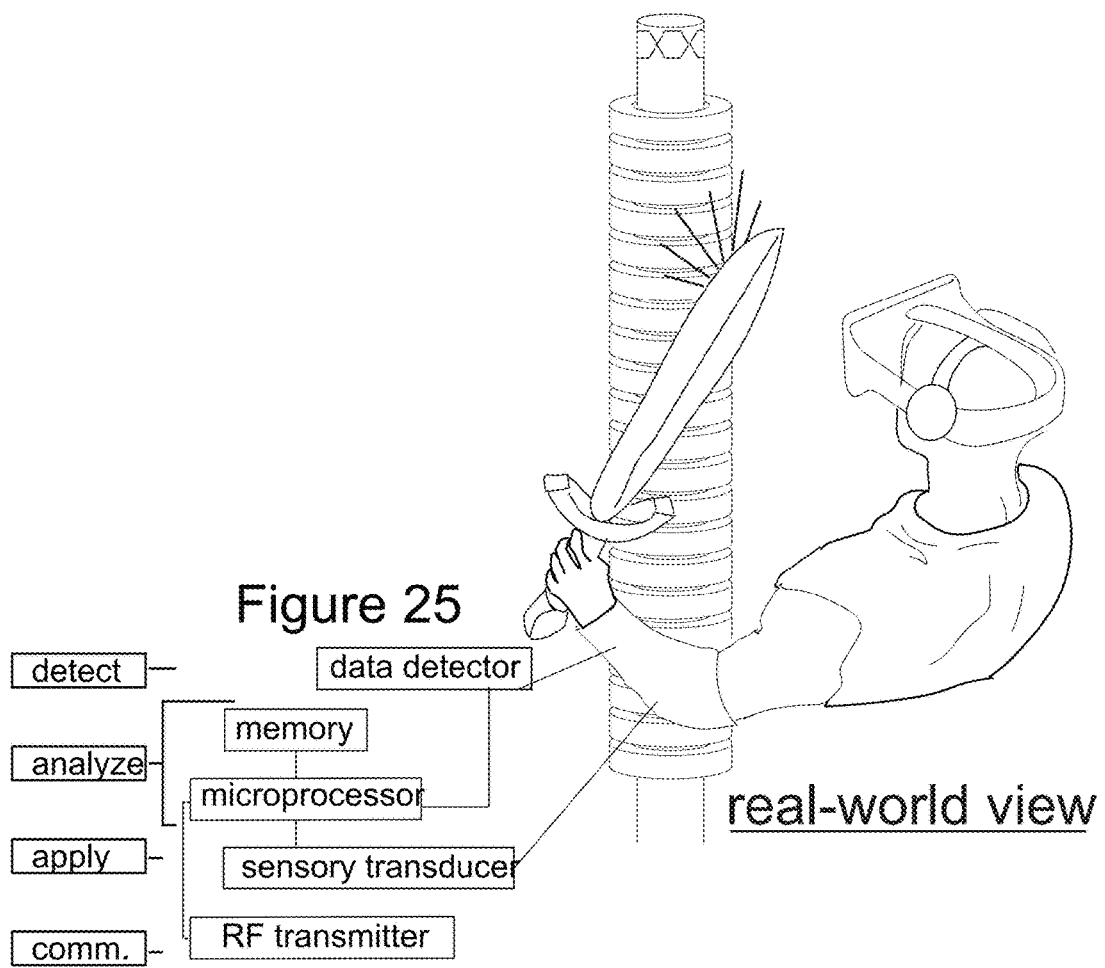
FIG. 25 shows the inventive virtual reality strike pole system in use in a sword game play.
Figure 26:
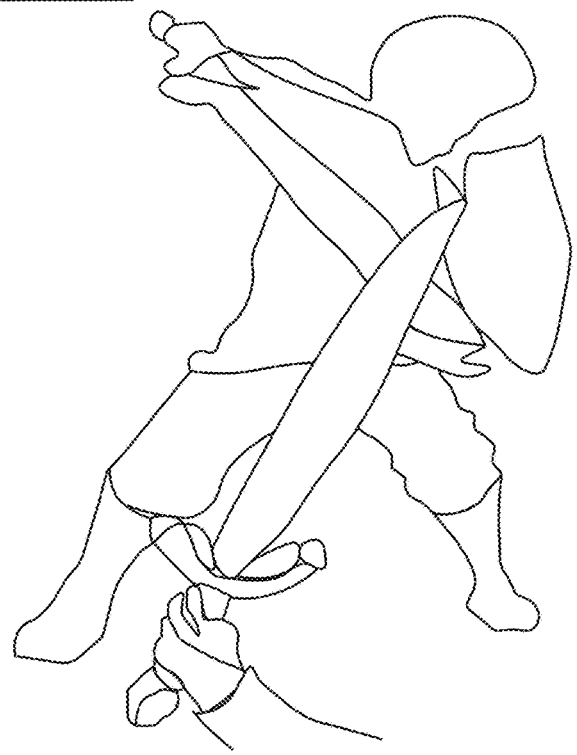
FIG. 26 shows the user's virtual reality view during the use of the inventive virtual reality strike pole system.
Figure 27:
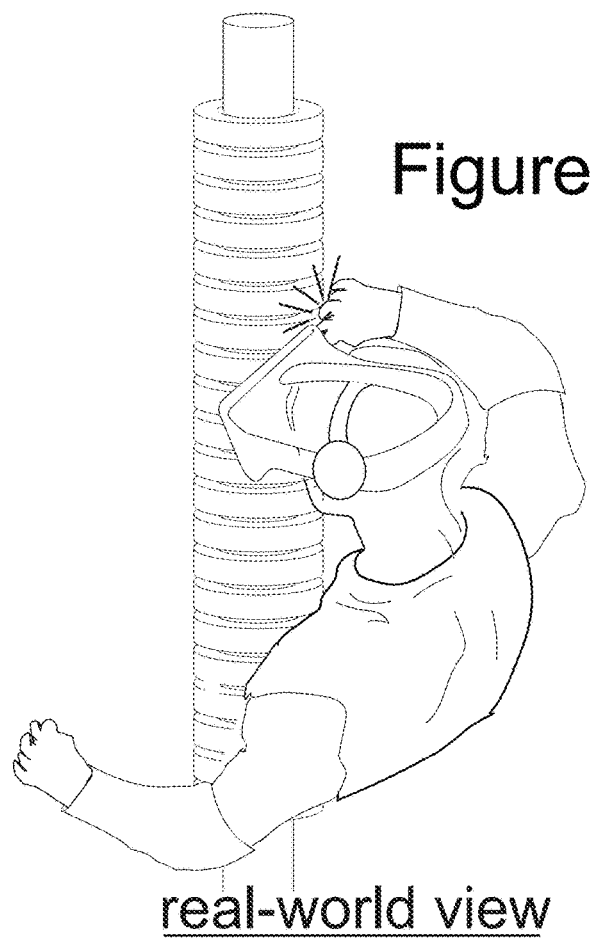
FIG. 27 shows the inventive virtual reality strike pole system in use as a boxing trainer.
Figure 28:
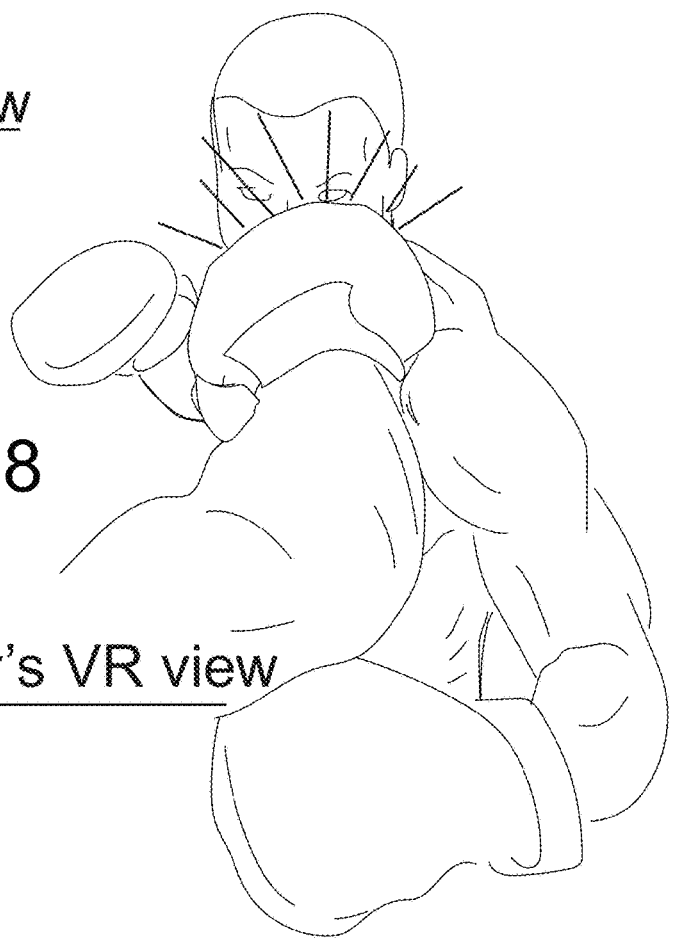
FIG. 28 shows the user's virtual reality view during the use of the inventive virtual reality strike pole system.

FIG. 20 shows a stack of pneumatic pressure transducers of an inventive virtual reality strike pole. FIG. 21 shows the inventive virtual reality strike pole having a stack of pneumatic pressure transducers and a position detecting system. FIG. 22 shows an exploded view of the inventive virtual reality strike pole. FIG. 23 shows the inventive virtual reality strike pole at a resting position. FIG. 24 shows the inventive virtual reality strike pole at an active position. FIG. 25 shows the inventive virtual reality strike pole system in use in a sword game play. FIG. 26 shows the user's virtual reality view during the use of the inventive virtual reality strike pole system. FIG. 27 shows the inventive virtual reality strike pole system in use as a boxing trainer. FIG. 28 shows the user's virtual reality view during the use of the inventive virtual reality strike pole system.

The inventive HHMI can be utilized as part of an interface called Virtuality™, which provides the next level of interface for VR and AR gaming. As an example embodiment, the player interacts in the real world with an impact sensing Strike Pole. The player's VR view includes the VR gaming sights and sounds, with real impacts and reactions to the impacts becoming an integral part of the gameplay. The Strike Pole offers variable resistance and movement through a Spring Joint. A striking surface includes pneumatic segments. The location, force and duration of a strike are detected. This information, along with data from IR and accelerometer position sensors provide the details needed to compute the physics of the gameplay so that the interactive VR experience is matched to the real-world strike.

The striking surface consists of a series of adjacent air-filled donuts. Each donut includes a pressure transducer that detects a change in the air pressure caused by a strike. A microprocessor uses the information from the pressure transducers and the position sensors to determine the physics of the Strike Pole. This information is transmitted via a wireless RF link to the gaming computer for use in determining the gameplay response to the strike and Strike Pole position.

The Strike Pole construction is modular for easy packaging and assembly. A flexible core fixed to a sturdy base supports a high-density foam sleeve around which are stacked the pneumatic segments. This construction allows the Strike Pole to whip in response to the strike. A Variable Resistance Spring Joint (VRSJ) is controlled by the microprocessor in response to wireless signals received from the gaming computer. The VRSJ controls the liveliness of the whipping Strike Pole to add controllability and adaptability to the particular VR gameplay action.

The Strike Pole combined with an action-filled VR game, such as boxing, provides the player with cardio exercise. The data of the strike location and pressure, the bending of the spring joint, and the accelerations and change of position of the Strike Pole are available to the gaming system through the wireless RF link so that the VR action matches the real world interaction between the player and the Strike Pole. For example, a VR boxing opponent bobs and moves in direct response to the strikes of the player. The harder the player strikes, the more active and unpredictable the VR opponent becomes.

A unique VR/2D gaming controller that includes haptic sensations applied to the fingertips to create the sensation of textures, hot, cold, slippery, etc. High Definition "Rumble Pack" as recently released Ninetendo Switch can be applied to the Haptic Controller. Accelerometer, IR tracking and pressure transducers complete the control and feedback implementation.

Figure 29:
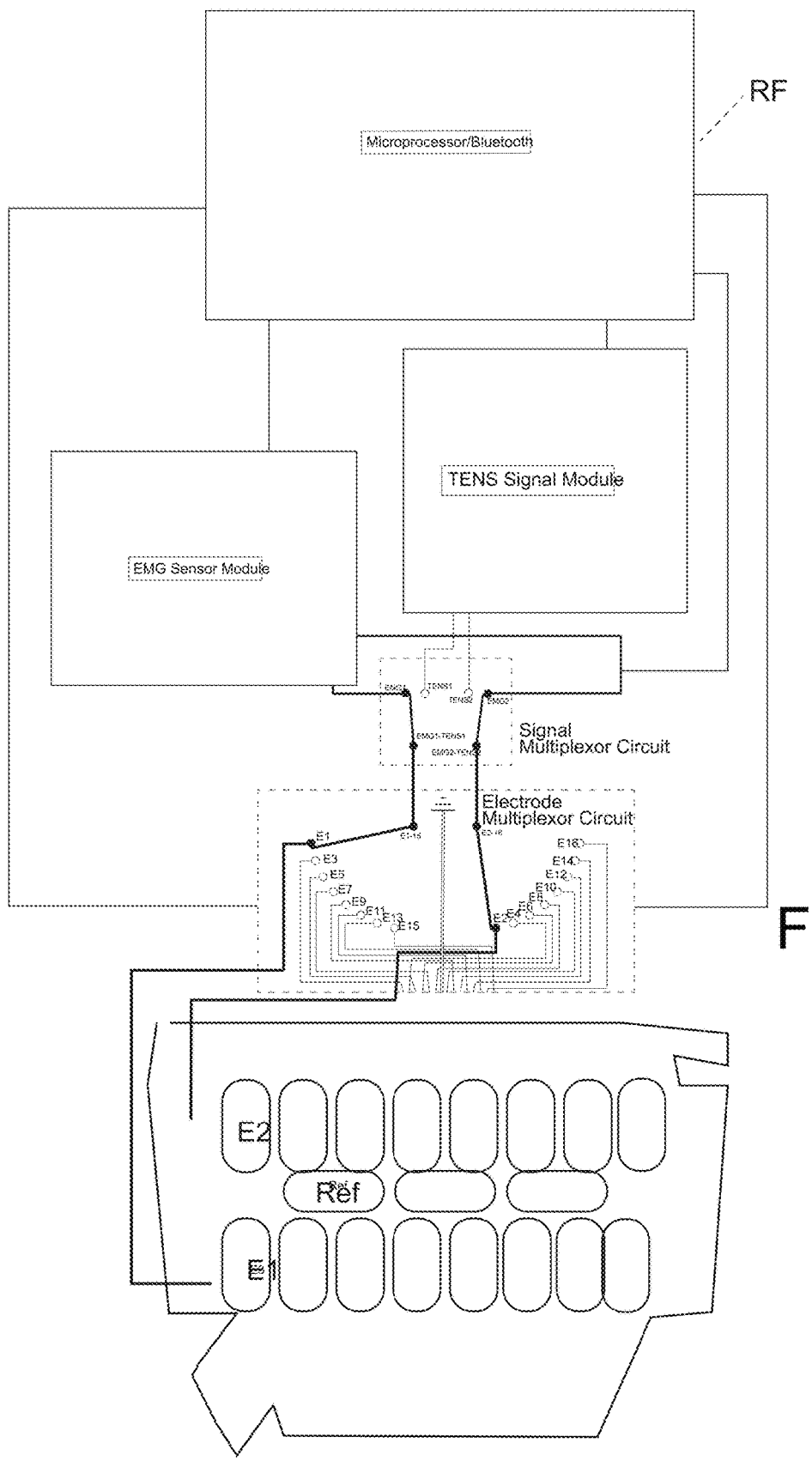
FIG. 29 illustrates the components of the inventive haptic human/machine interface.
Figure 30:
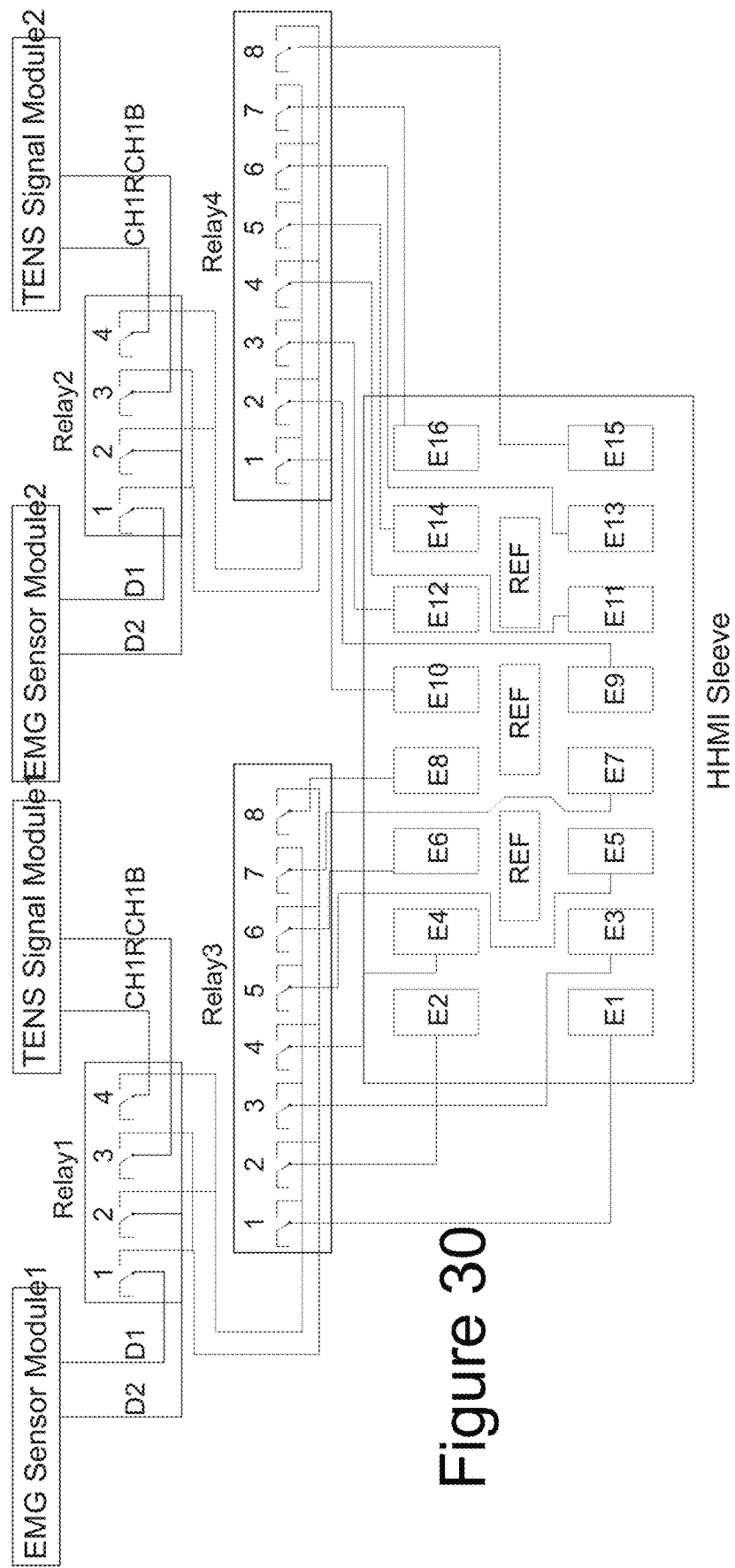
FIG. 30 illustrates an exemplary circuit construction for detecting and applying electrical signals from and to the user through the same electrodes and/or connection leads and/or electronic components.

FIG. 29 illustrates the components of the inventive haptic human/machine interface. FIG. 30 illustrates an exemplary circuit construction for detecting and applying electrical signals from and to the user through the same electrodes and/or connection leads. The exemplary embodiments of the HHMI empower wearable electronics with the capability to detect, analyze and apply the electrical signals of the human body. Unlike any other wearable architecture, the large array of small addressable electrodes create easy user-customization, calibration and change in the use of the garment. Location and placement of the garment on the body does not have to be precise, can shift around, and automatically accommodates for different sizes and user physiologies.

Uses of the HHMI wearable electronics include the secure aggregation of biometric data, nonopioid pain relief, accelerated learning, sports augmentation and training, and military applications such as remote unmanned vehicle sensing and control. As shown, in accordance with an aspect of the invention a housing is provided. A plurality of individually addressable electrodes is supported by the housing. The individually addressable electrodes are for at least one of applying stimulation electrical signals to skin of a user and detecting biometric electrical signals from the skin of the user. At least one of a signal detector for detecting the biometric electrical signals and a signal generator for generating the stimulation electrical signals are provided. An electrode multiplex circuit addresses the plurality of individually addressable electrodes by at least one of routing the biometric electrical signals from the skin of the user through more than one of the plurality of individually addressable electrodes to the signal detector and routing the stimulation electrical signals from the signal generator through more than one of the plurality of individually addressable electrode to the skin of the user. A microprocessor controls least one of the signal detector, the signal generator, and the electrode multiplex circuit.

A plurality of individually addressable electrodes can be disposed for receiving biometric electrical signals from motor units underlying the skin of a user. The plurality of individually addressable electrodes may have a biometric signal detection electrodes disposed in pairs that approximately line up with the long axis of muscles in the forearm of a user, along with reference electrodes disposed between the electrode pairs. FIG. 29 shows an HHMI for applying electrical stimulation of the nerves and/or muscles of a user (commonly known as transcutaneous electrical nerve stimulation (TENS), or electrical muscle stimulation (EMS)) to cause an involuntary muscle contraction that causes an induced movement and change in position of a body part of the user in response to the applied electrical signal. This computer controlled involuntary movement is synchronized with the application of a computer controlled visual sensory cue so that two processing areas of the user's brain are synchronously, simultaneously stimulated. This synchronized, simultaneous stimulation of the processing areas is effective for building up muscle memory to strengthen the user's brain and nervous functions that control the change in the position of the user's body part.

The microprocessor can control the electrode multiplex circuit to route the biometric electrical signals from the skin of the user sequentially through more than one of the plurality of individually addressable electrodes to the signal detector. The microprocessor can control the electrode multiplex circuit to route the biometric electrical signals from the skin of the user simultaneously through more than one of the plurality of individually addressable electrodes to the signal detector. The microprocessor can control the electrode multiplex circuit to route the stimulation electrical signals from the signal generator simultaneously through more than one of the plurality of individually addressable electrodes to the skin of the user. The microprocessor can control the electrode multiplex circuit to route the stimulation electrical signals from the signal generator sequentially through more than one of the plurality of individually addressable electrodes to the skin of the user. The microprocessor can control the electrode multiplex circuit to route the stimulation electrical signals from the signal generator simultaneously through more than one of the plurality of individually addressable electrodes to the skin of the user.

Figure 31:
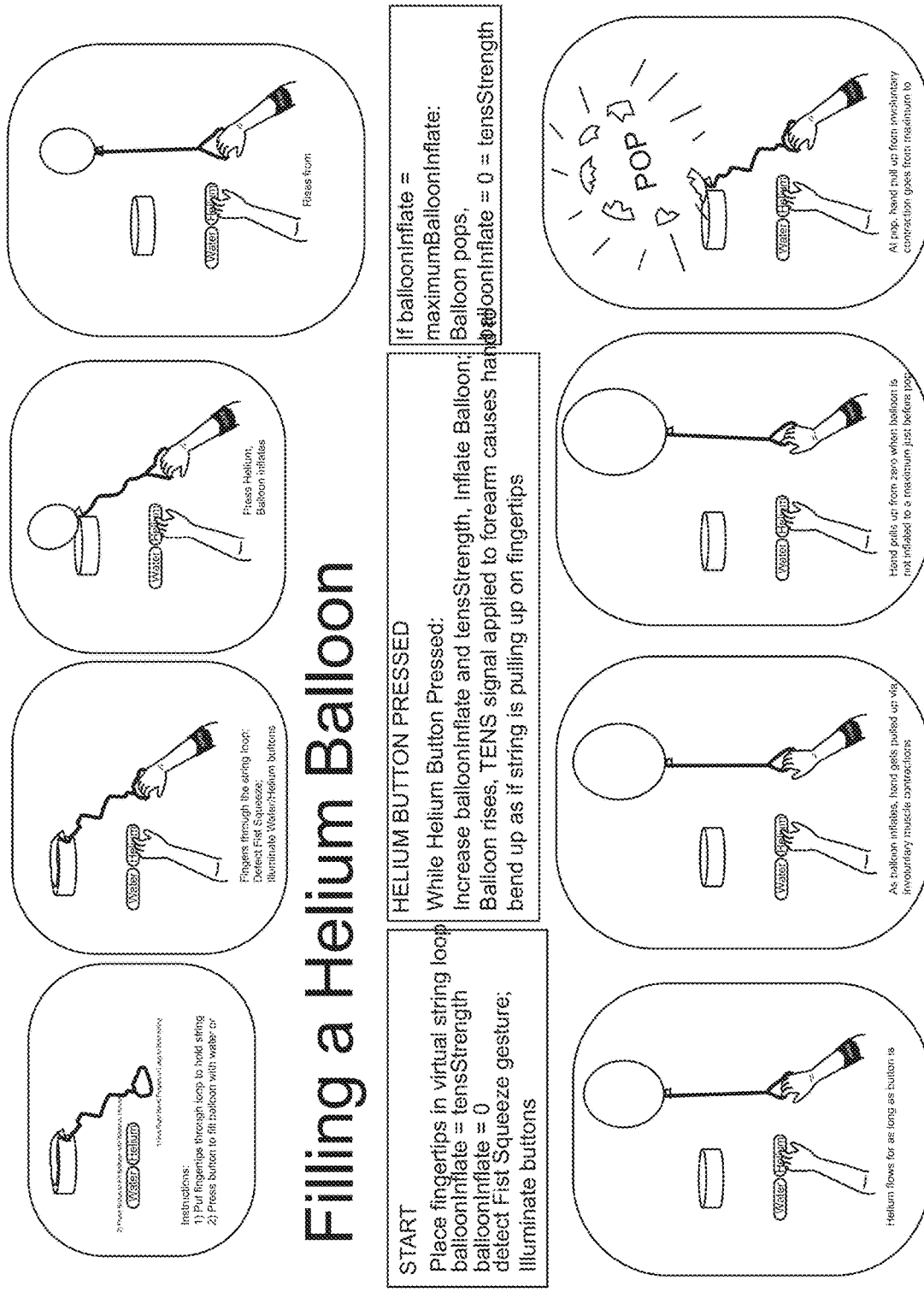
FIG. 31 illustrates a virtual reality interactive balloon demo showing the interaction with a virtual visual representation of a balloon as a virtual object synchronized with the application of involuntary muscle contractions.
Figure 32:
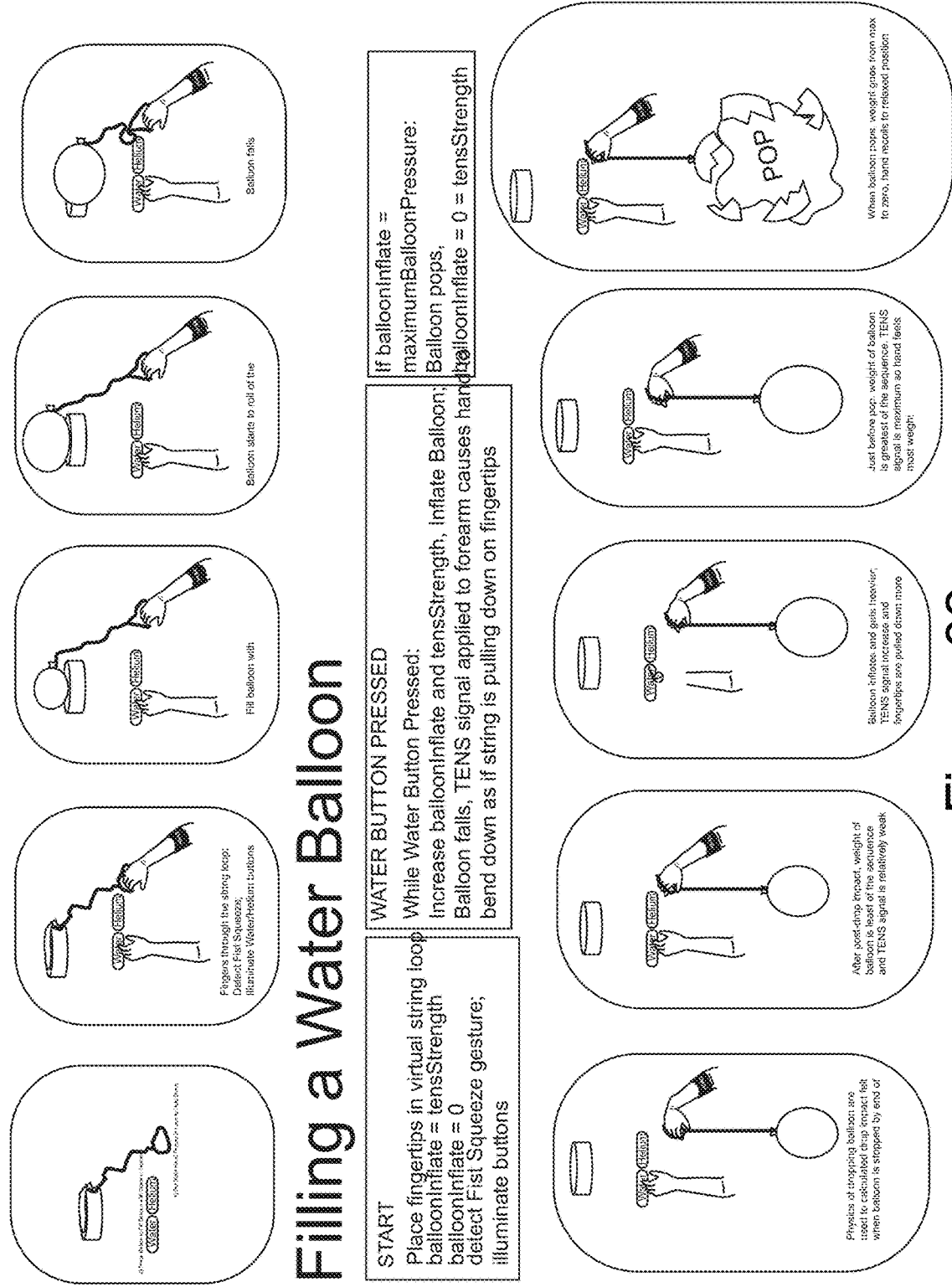
FIG. 32 illustrates the virtual reality interactive balloon demo showing the interaction with a virtual visual representation of a virtual object synchronized with the application of involuntary muscle contractions creating haptic and proprioception applied sensory cues.
Figure 33:
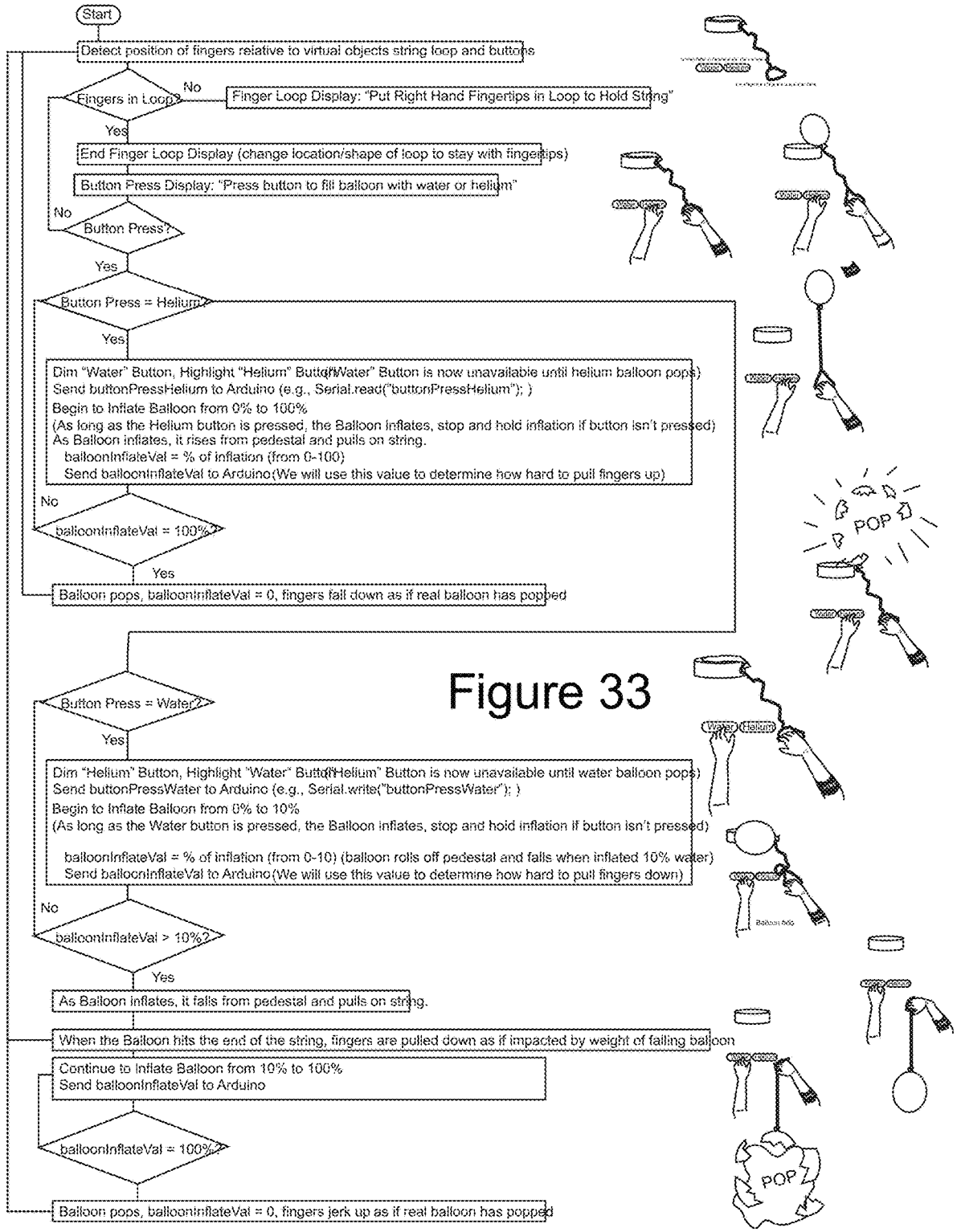
FIG. 33 is a flowchart of the virtual reality interactive balloon demo.
Figure 34:
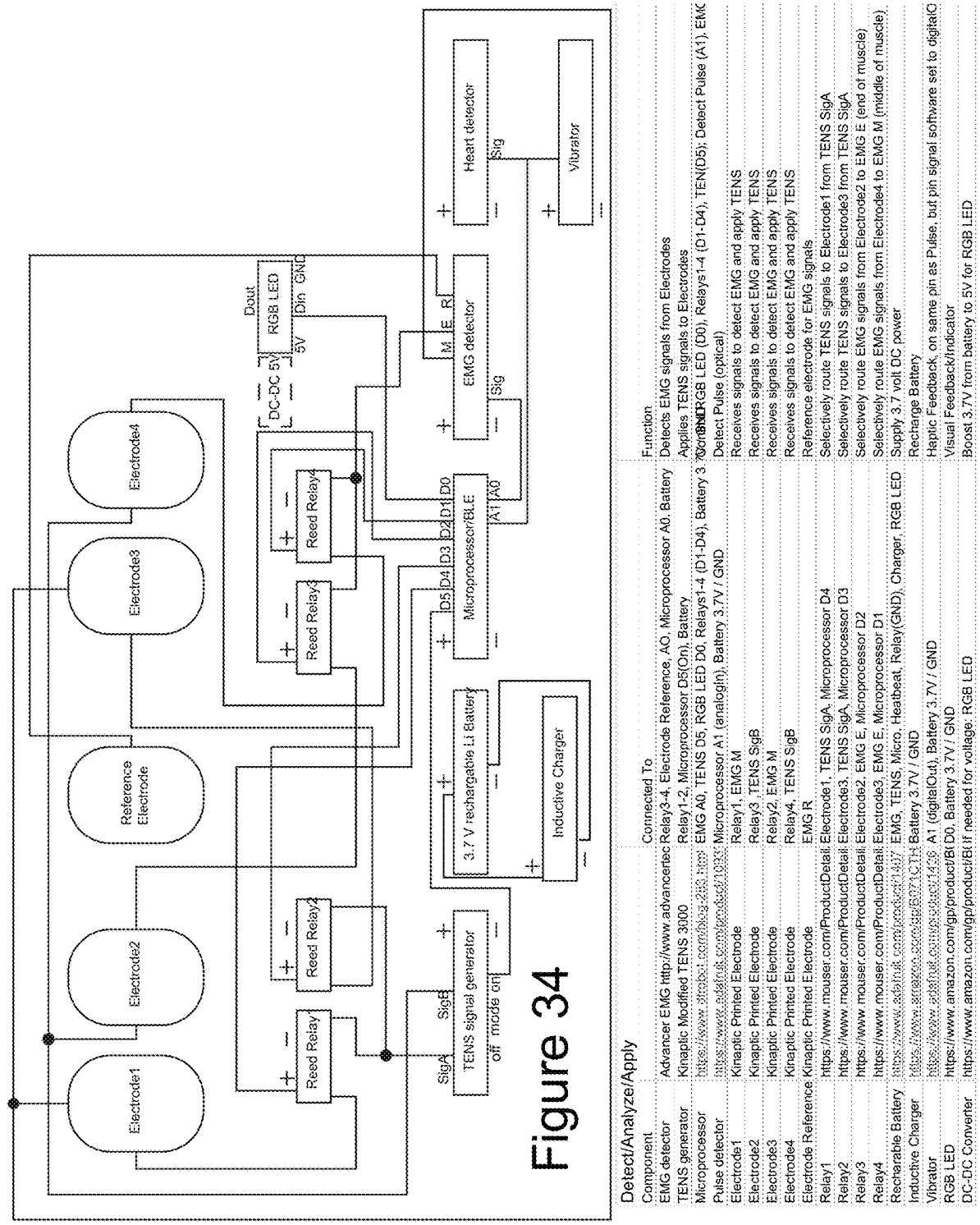
FIG. 34 illustrates the general circuit components and construction of an inventive haptic human/machine interface that can be used with the virtual reality interactive balloon demo.
Figure 35:
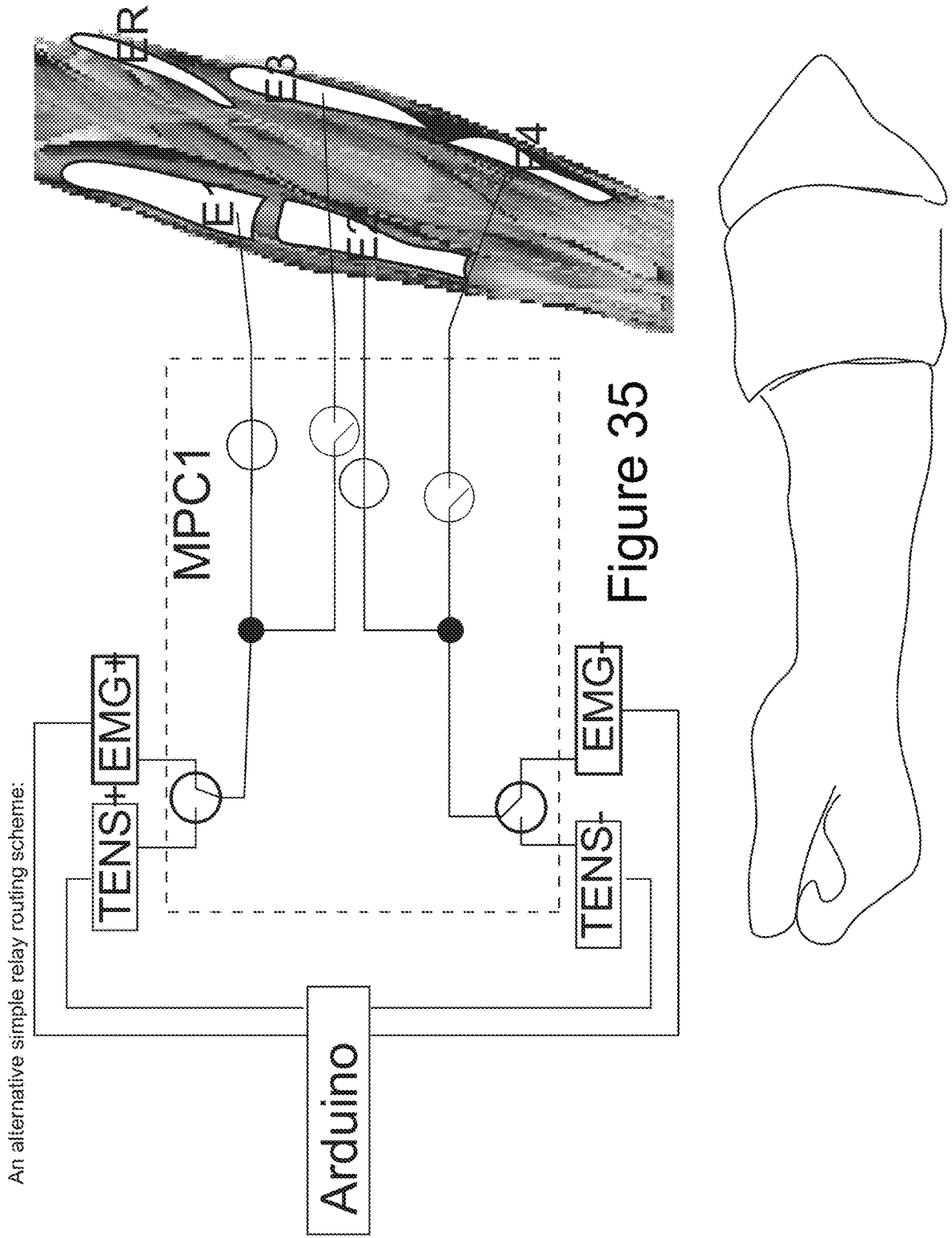
FIG. 35 illustrates the inventive haptic human/machine interface for selectively applying transcutaneous electrical nerve stimulation and selectively detecting electromyography through the same electrodes and/or circuit components.

FIG. 31 illustrates a virtual reality interactive balloon demo showing the interaction with a virtual visual representation of a balloon as a virtual object synchronized with the application of involuntary muscle contractions. FIG. 32 illustrates the virtual reality interactive balloon demo showing the interaction with a virtual visual representation of a virtual object synchronized with the application of involuntary muscle contractions creating haptic and proprioception applied sensory cues. FIG. 33 is a flowchart of the virtual reality interactive balloon demo. FIG. 34 illustrates the circuit components and construction of an inventive haptic human/machine interface that can be used with the virtual reality interactive balloon demo. FIG. 35 illustrates the inventive haptic human/machine interface for selectively applying transcutaneous electrical nerve stimulation and selectively detecting electromyography through the same electrodes and/or circuit components.

The balloon demo is an effective but simple demo that shows the ability to 1) detect an EMG signal from a user's forearm to initiate a command; 2) show movement of the user's hand in VR; and 3) apply a TENS signal to the user's forearm to cause the user's hand to involuntarily move up and down depending on the interaction with a virtual object. The demo fills a virtual balloon with helium to pull the user's fingertips up, and fills the virtual balloon with water to pull the user's fingertips down. A VR headset shows the virtual balloon, and LeapMotion is used to detect the position of the user's arm, hand and fingers. An HHMI sleeve detects a simple hand gesture to start the interaction and to provide the haptic feedback of the interaction with the virtual balloon. The HHMI sleeve has an Arduino controller, with code to respond to a change of state of an Arduino pin (e.g., LOW to HIGH) when an EMG signal is detected. The code also indicates when a virtual button is pressed (WATER or HELIUM) and provides a signal to another Arduino pin that depends on the amount of inflation of the virtual balloon. A balloon inflation value is used to determine the strength of the applied TENS signal which causes the fingertips to involuntarily go up or down.

Figure 36:
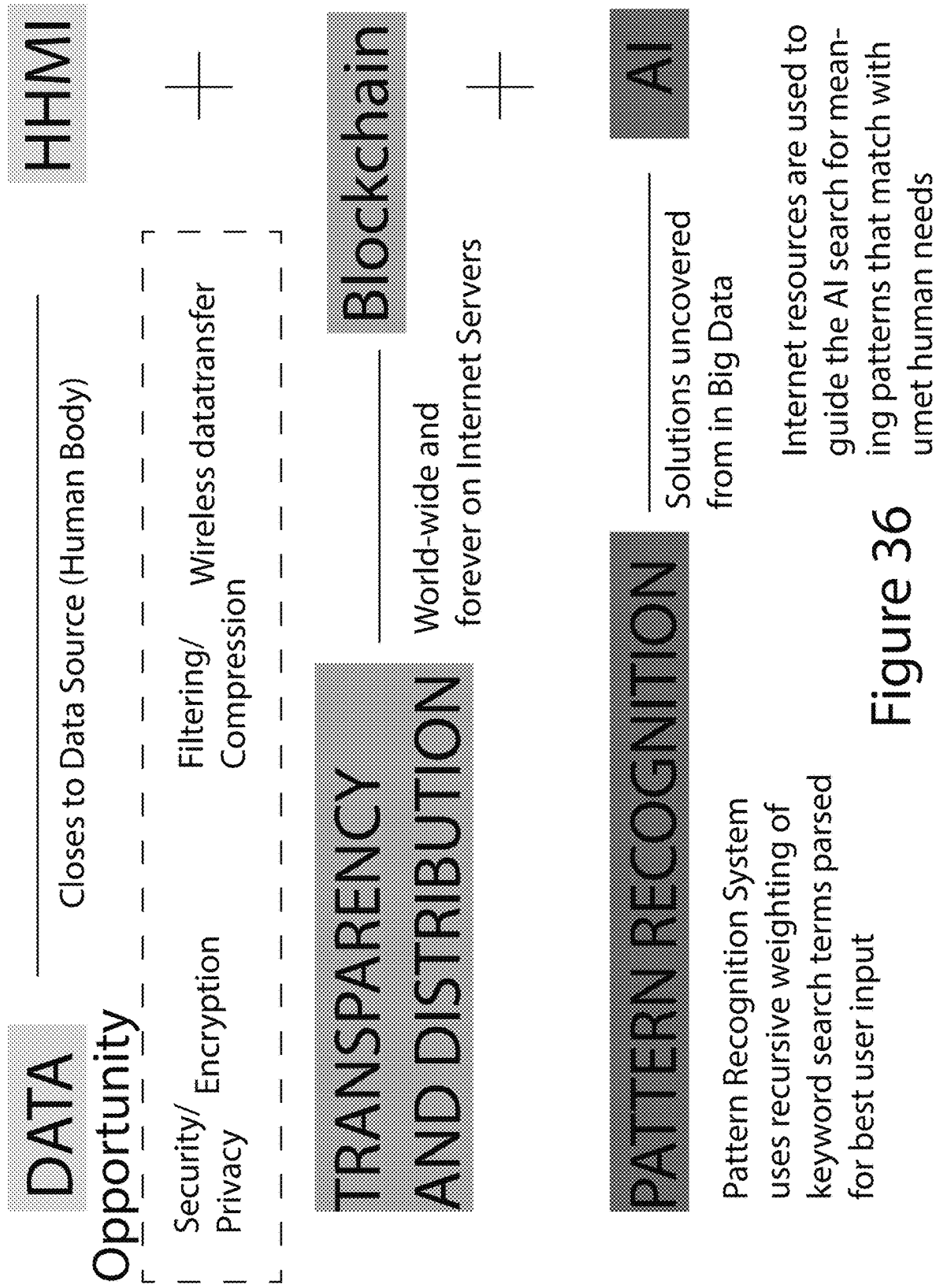
FIG. 36 illustrates an inventive system for biometric data collection, blockchain-based distribution and artificial intelligence pattern recognition using an embodiment of the inventive human/machine interface.
Figure 37:
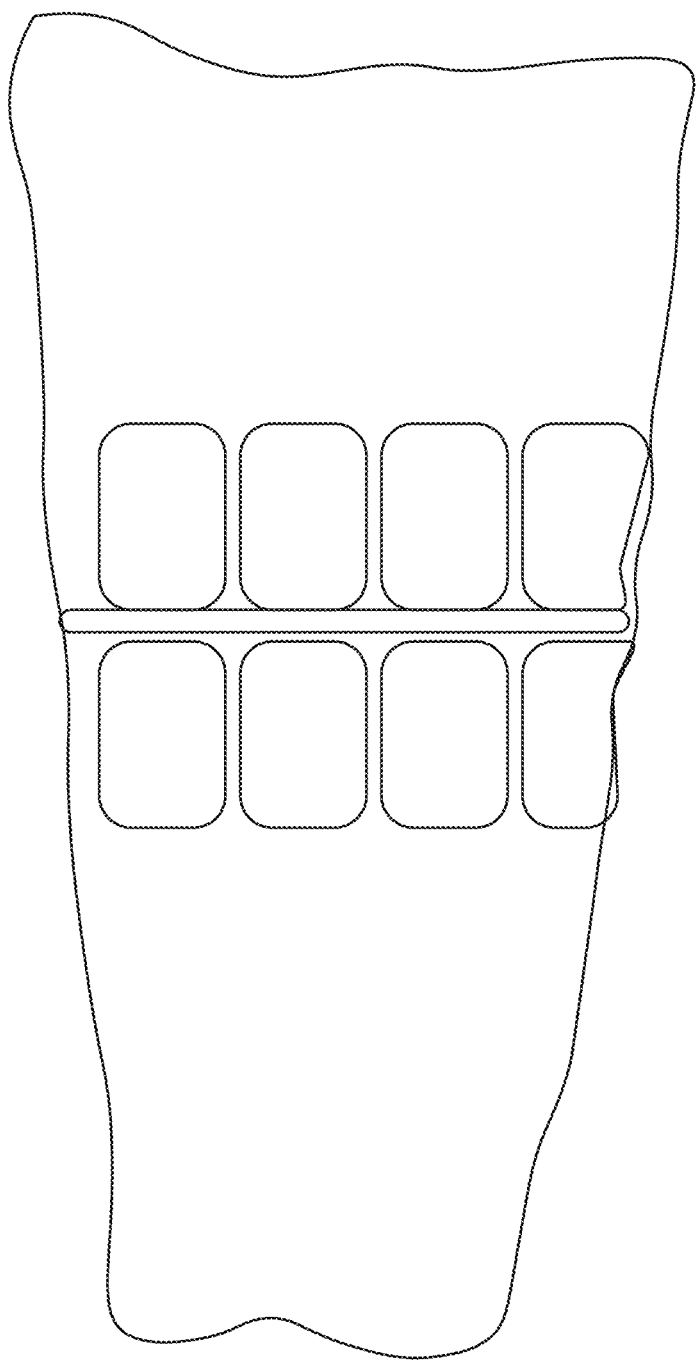
FIG. 37 shows an embodiment of an inventive wearable electronic forearm sleeve having individually addressable electrodes.

FIG. 36 illustrates an inventive system for biometric data collection, blockchain-based distribution and artificial intelligence pattern recognition using and embodiment of the inventive human/machine interface. FIG. 37 shows an embodiment of an inventive wearable electronic forearm sleeve having individually addressable electrodes.

A very important use of the HHMI platform is to contribute enabling technologies and products to create a cradle-to-grave system that obtains biometrics from a user, forever secures the data integrity, privacy, and access, and makes this secured data available to feed big data pattern recognition to improve global human health.

There are uses of this biometric/BC/AI model that apply to other emerging sensor-based IoT systems for uses including monitoring crop growth, sanitation, and mitigating infant mortality in developing countries.

With regards to the biometric/BC/AI platform, the general premise is that soon biometrics will be collected from much of the population all day/every day. Over time (eventually, a lifetime) this data will be far more valuable at predicting and preventing disease and other health issues than our yearly physical examinations. This health advantage will be very compelling and cause more sales and use of wearable electronics for collecting more biometrics more of the time.

For population studies, this data will be invaluable to medical researchers, NGOs and government organizations. A distributed ledger technology can be adapted to make this data available, in bulk, as anonymous, accurate information (e.g., only demographics, nothing to identify the individual) while also making it securely and permanently stored to be analyzed by a trusted receiver (e.g., a health care provider) over the lifetime of the individual. The content and quantity of the individual's data made available can be adjusted depending on the data recipient.

The HHMI can be used to provide secure and accurate open-source access to a vast amount of collected biometric data to researchers around the world. When many people are wearing some form of biometric detection technology every day (for example, a "smart" T-shirt or underwear), it may not be efficient to put online, for example, every heartbeat, so some filtering and compression of collected data is needed. The biometric data can be filtered to detect anomalies or potential anomalies in the collected biometric data. There also needs to be a data security layer as close to the source (the user) as possible. The HHMI technology platform uses wearables, blockchain and AI to collects biometric data, such as heartbeat and sweat chemistry from a living organism, like a human or a pet, anonymously and securely store that data using block chain technology, and use AI to look for patterns in the data to determine health aspects of the population such as heart disease and diabetes. Using the HHMI, biometric data can be used for authentication, for example, the HHMI configured as underwear is a great target garment for the wearable electronic. A detected heartbeat signature that is unique to the individual can be used for secure identification, with near field communication used to send the heartbeat signature from the wearable electronic through a WiFi or cellular connection to an online server to securely authenticate the user.

Blockchain distributed ledger is highly valued technology that could store copious biometric data and make it available forever, transparently and securely. AI agents connected to the cloud could be finding patterns in this biometric data generated by every human body. These patterns unlock opportunities for vast improvements in personal and global population health. It's all about the data.

The HHMI can be formed in a number of scalably manufacturable clothing configurations with a large array of many individually addressable electrodes connected to a single detection and application electronic unit. The architecture of the HHMI is adapted to mass production as a roll-to-roll manufactured printed electronic garment with embedded sensors and transducers. Applications include biometric sensing for health and fitness, stroke rehabilitation, tremor mitigation and pain relief. The Blockchain distributed ledger technology is adapted to make this data available, in bulk, as anonymous, accurate information (only demographics, nothing to identify the individual) while also making it securely and permanently stored to be analyzed by a trusted receiver (e.g., health care provider) over the lifetime of the individual.

The HHMI technology can be used to provide secure and accurate open-source access to a vast amount of collected biometric data to researchers around the world. The HHMI wearable electronic garments provide bi-directional capabilities to detect/analyze/apply signals to/from the human body and distributes a large array of individually addressable electrodes and sensors, enabling a single sensor or signal generator to service many electrodes, with multiple small electrodes forming physiology matching patterns.

Artificial Intelligence Agents are becoming adept at finding hidden patterns in copious datasets. These hidden patterns can be used to assist researchers in drug discovery, medical device R&D, looking for biomarkers in electrical and chemical activities of the human body. There are a host of other biometric and environmental data that could be useful for AI for R&D, some of which have not even been conceived yet. But, it all starts with the data. There is not yet an adequate wearable electronic that can be used to easily capture and make available the full range of biometrics from large population samples.

The HHMI wearable electronic product architecture, manufacturing methods, and applications, can be used for capturing high fidelity biometric data from the human body. The HHMI advantages include lower cost, easier to use form factor, wearable products with wide a range of sensors and embedded AI software. The HHMI bi-directional detect/analyze/apply enables proactive responses such as active transdermal drug delivery and transcutaneous electrical nerve stimulation automatically applied or remotely triggered by a monitoring physician. Biometric data can be captured and transmitted continuously or at selected times with data access provided directly to care-provider, enabling early diagnosis and ongoing monitoring, and to the researcher to gain valuable insights and assistance through AI analysis. This data detection is direct from the human body and is provided for Blockchain and AI database collection, access and analysis. The HHMI wearable electronic for biometric capture is adapted to mass production as a roll-to-roll manufactured printed electronic garment with embedded sensors and transducers. In addition to AI assisted R&D, applications also include biometric sensing for health and fitness, stroke rehabilitation, tremor mitigation and pain relief.

The HHMI wearable electronic provides secure and accurate encrypted and/or open-source access to a vast amount of collected biometric data to R&D researchers. The HHMI wearable electronic garments provide bi-directional capabilities to detect/analyze/apply signals to/from the human body.

Figure 38:
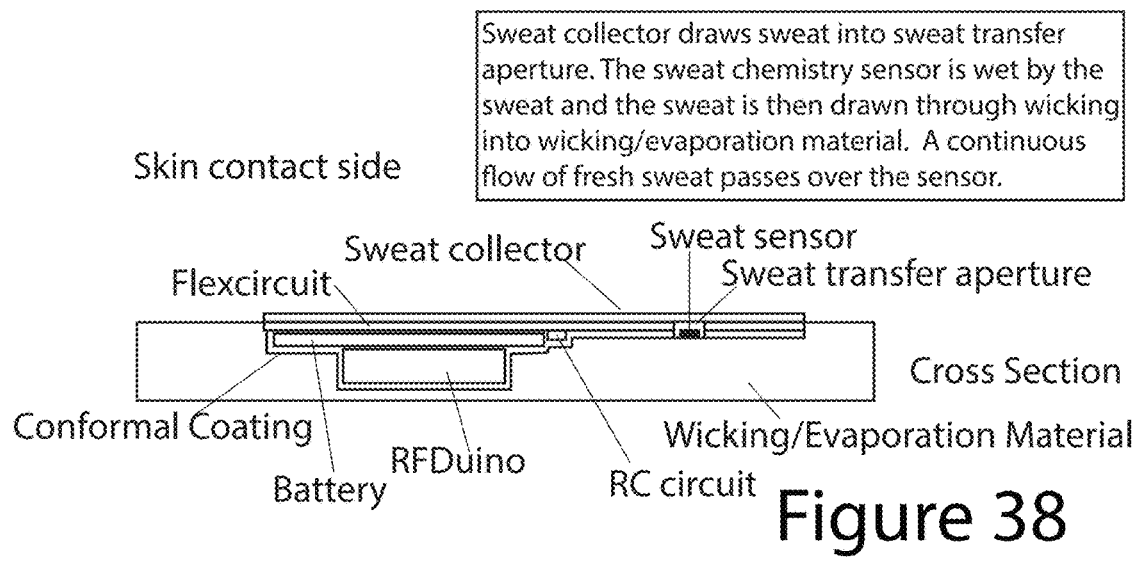
FIG. 38 shows a cross section of an inventive wearable electronic sweat chemistry sensor.
Figure 39:
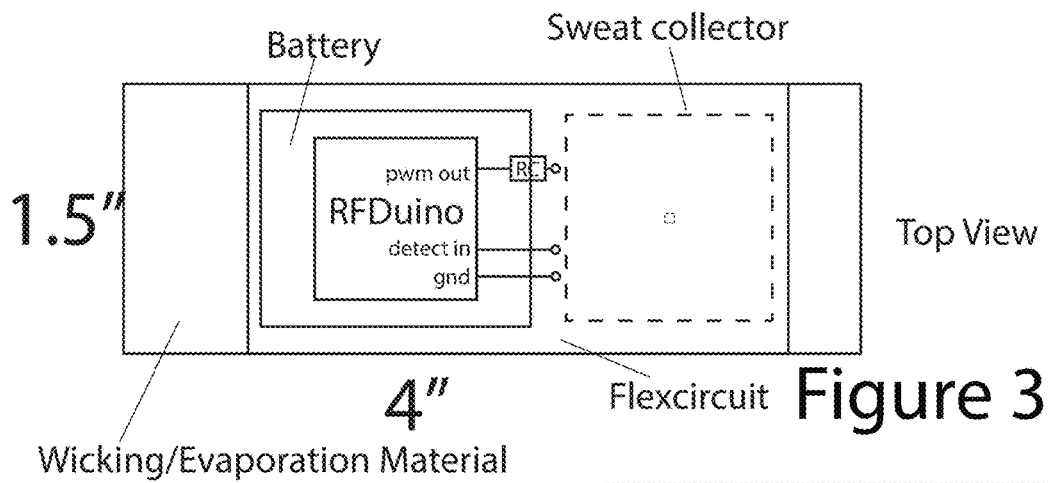
FIG. 39 shows a top view of the inventive wearable electronic sweat chemistry sensor.
Figure 40:
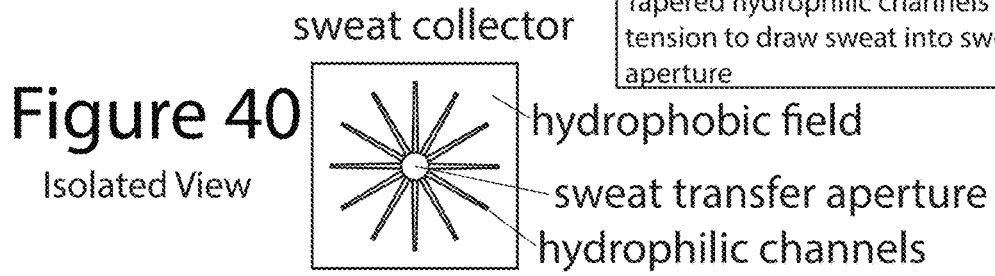
FIG. 40 is an isolated view showing a sweat collector of the inventive sweat chemistry sensor.
Figure 41:
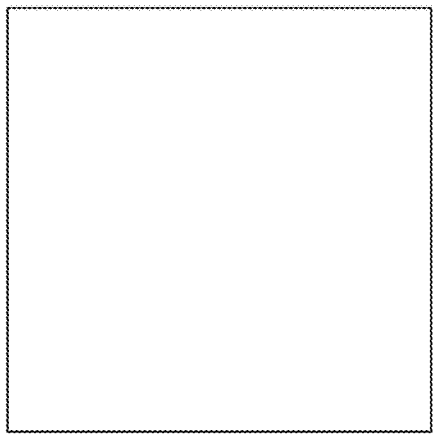
FIG. 41 shows a first step in forming a sweat collector having a flow through structure.
Figure 42:
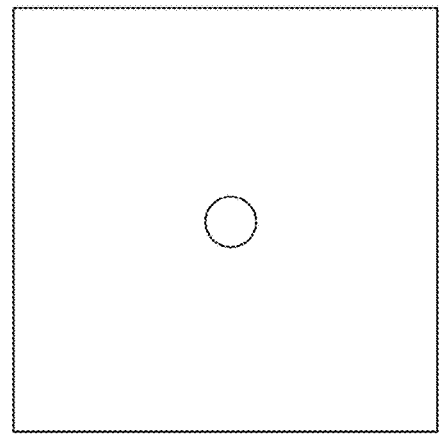
FIG. 42 shows a second step in forming a sweat collector having a flow through structure.
Figure 43:
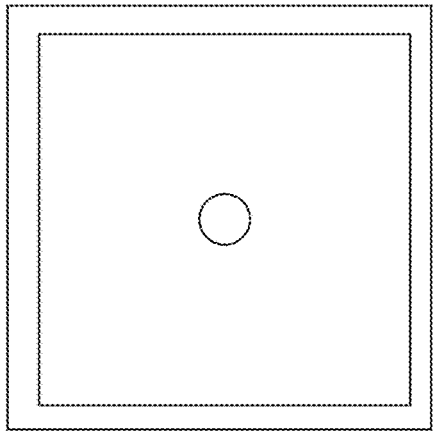
FIG. 43 shows a third step in forming a sweat collector having a flow through structure.
Figure 44:
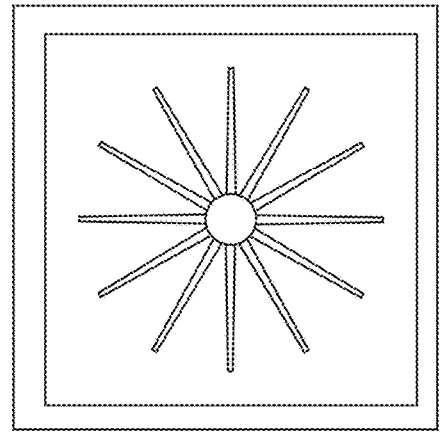
FIG. 44 shows a fourth step in forming a sweat collector having a flow through structure.
Figure 47:
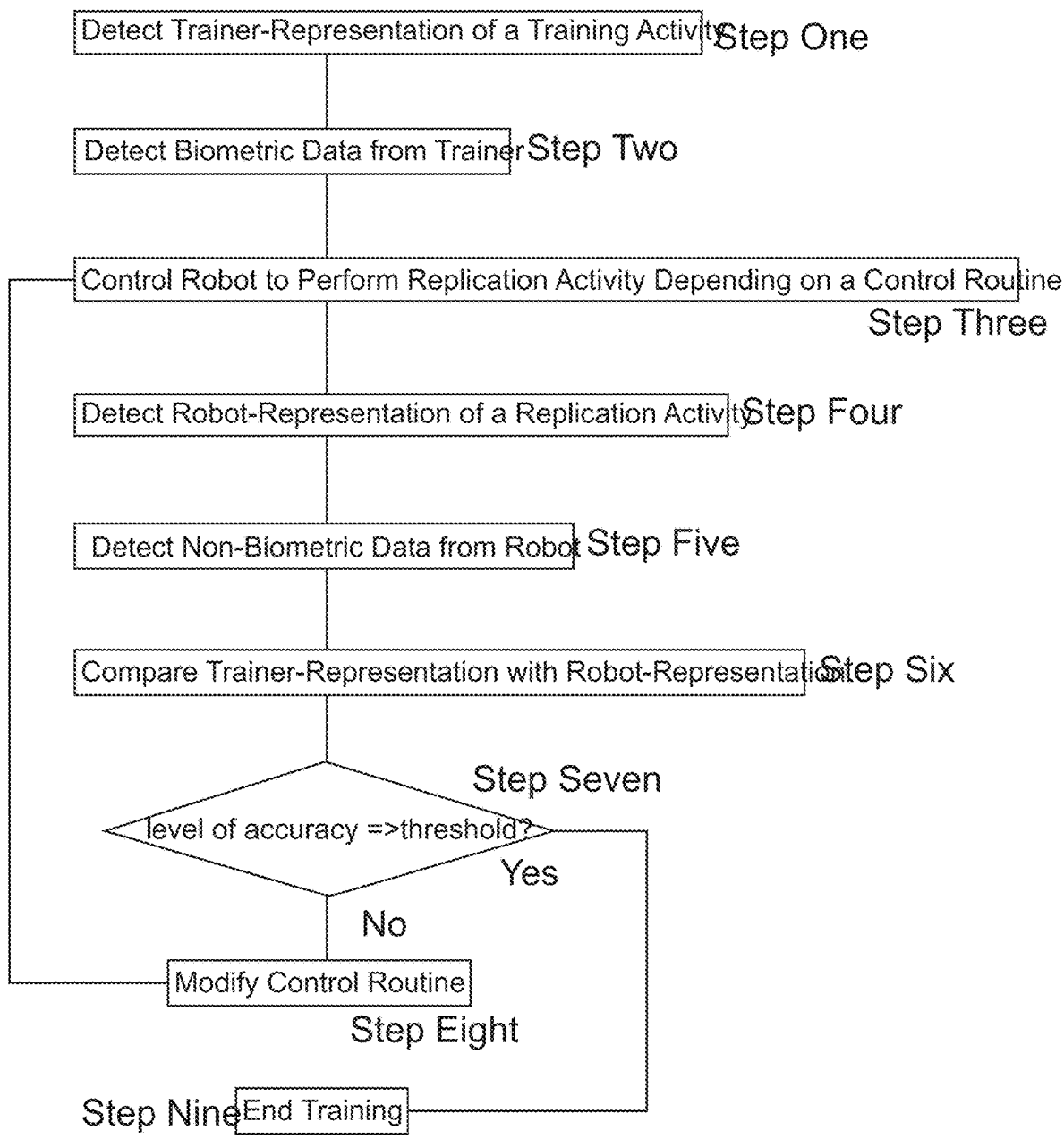
FIG. 47 is a flowchart showing a use of the inventive wearable electronic for robot training.

FIG. 38 shows a cross section of an inventive wearable electronic sweat chemistry sensor. A sweat collector draws sweat into a sweat transfer aperture. The sweat chemistry sensor is wet by the sweat and then the sweat is drawn through wicking into wicking/evaporation materials. A continuous flow of fresh sweat passes over the sensor. FIG. 39 shows a top view of the inventive wearable electronic sweat chemistry sensor. FIG. 40 is an isolated view showing a sweat collector of the inventive sweat chemistry sensor. A hydrophobic field encourages sweat to bead and migrate to hydrophilic channels. Tapered hydrophilic channels use surface tension to draw sweat into the sweat transfer aperture. FIG. 41 shows a first step in forming a sweat collector having a flow through structure. Hydrophobic and hydrophilic screen printable inks are available from companies such as Cytonix and Wacker. FIG. 42 shows a second step in forming a sweat collector having a flow through structure. FIG. 43 shows a third step in forming a sweat collector having a flow through structure. FIG. 44 shows a fourth step in forming a sweat collector having a flow through structure. FIG. 46 illustrates an inventive wearable electronic garment having a sweat chemistry sensor and a long service before saturation waistband.

Any water-soluble component in the blood can be detected through sweat chemistry analysis. Lactate, Glucose and Urea are three important blood chemistry measurements. Lactate is the output of the anaerobic system; after that it performs its most important function. It is the main fuel for the aerobic system during competition and much of training. Lactate is a major fuel source for the heart and the brain as well as skeletal muscles during strenuous efforts.

Measuring lactate is a way of assessing how strong each energy system is, or essentially how well-conditioned the athlete/soldier is at a specific point in time. No other measure provides this information. Measuring lactate is the best way to assess the conditioning level of an athlete/soldier during training and prior to a competitive event or mission. Theoretically the best place to measure lactate to see what is happening during exercise is in the muscles themselves. But this is not currently possible without doing muscle biopsies. There may be a particular advantage to multiple low cost sweat chemistry sensors incorporated in a multi-pixel sensing array for measuring the lactate produced by specific muscles.

Various modifications and adaptations to the foregoing exemplary embodiments of this invention may become apparent to those skilled in the relevant arts in view of the foregoing description, when read in conjunction with the accompanying drawings. However, any and all modifications will still fall within the scope of the non-limiting and exemplary embodiments of this invention.

Furthermore, some of the features of the various non-limiting and exemplary embodiments of this invention may be used to advantage without the corresponding use of other features. As such, the foregoing description should be considered as merely illustrative of the principles, teachings and exemplary embodiments of this invention, and not in limitation thereof.

What is claimed is:

1. A wearable electronic, comprising:
   a woven fabric formed from a plurality of interlaced threads, the plurality of interlaced threads comprising a plurality of warp threads interlaced with a plurality of weft threads, the woven fabric having a top face and a bottom face;
   a plurality of conductive threads included among the plurality of interlaced threads at predetermined intervals and interlacing angles to provide a pattern of respective connection locations, wherein the respective connection locations are located at regular intervals on at least one of the top face and the bottom face of the woven fabric, the plurality of conductive threads being interlaced in the warp threads and the weave threads so that at the regular intervals a connection area is disposed having a first, a second, a third, a fourth, a fifth and a sixth conductive thread, where the first conductive thread provides a ground connection portion, the second conductive thread provides a power connection portion, the third conductive thread provides a data-in connection portion, the fourth conductive thread provides a data-out connection portion, the fifth conductive thread provides a first electrical apply connection and the sixth conductive thread for provides a second electrical apply connection, wherein the predetermined intervals and interlacing angles of the warp and weft of the plurality of interlaced threads disposes the first, second, third, fourth, fifth and sixth conductive threads so that the respective connection locations are each located at corresponding vertices of a plurality of hexagonal connection areas located at the regular intervals, wherein a plurality of hexagonal connection areas are located at the regular intervals on at least one of the top and the bottom face of the woven fabric.

2. The wearable electronic according to claim 1; wherein the conductive threads are insulated with a conductive core.

3. The wearable electronic according to claim 1; wherein the conductive threads include at least one conductive thread having a semiconductor composition.

4. A wearable electronic according to claim 1; further comprising at least one functional element connected to at least one of the connection portions of at least one of the conductive threads at at least one of the plurality of connection areas.

5. The wearable electronic according to claim 1, wherein the fifth conductive thread and the six conductive thread carry an electrical muscle stimulation signal to apply an electrical signal to at least one of muscles and nerves of a user to induce involuntary muscle contractions to cause movement and change a position of at least one body part of the user; wherein the electrical signal is applied as the first sensory cues to the user to cause the involuntary muscle contraction to cause movement and change the position of the at least one body part of the user in response to the electrical signal applied to the user.

6. The wearable electronic according to claim 5, further comprising a display for providing visual sensory cues to the user to provide a virtual visual indication to the user of the change in position of the at least one body part so that the change in position of the at least one body part is virtually visually indicated in synchronization with the change in the position of the at least one body part.

7. The wearable electronic according to claim 6; wherein the at least one body part is at least one leg of the user; wherein the visual sensory cue includes a visual scene related to riding of the bicycle; and wherein the applied electrical signal causes the induced movement of the at least one leg synchronized with the visual sensory cue for building up muscle memory to strengthen the user's brain and nervous functions that control the change in the position of the at least one leg.

8. The wearable electronic according to claim 7, further comprising a sensory cue generator for generating a second sensory cue capable of being perceived by the user, the second sensory cue being dependent on at least one of a recorded non-biometric data and a recorded biometric data, the second sensory cue being effective for stimulating at least a second processing area of the brain of the user, the second sensory cues being synchronized with the visual sensory cues so that the second processing area is stimulated with the second sensory cue in synchronization with the visual sensory cue stimulating a visual processing area, wherein the synchronized stimulation of the visual processing area and the second processing area is effective for building up muscle memory to strengthen the user's brain and nervous functions.

9. The wearable electronic according to claim 6; wherein the video display device comprises at least one an augmented or virtual reality headset, a computer monitor, a television, a smart phone display or a personal information device display.

10. A wearable electronic fabric comprising a woven fabric formed from a plurality of interlaced threads, the plurality of interlaced threads comprising a plurality of conductive threads and a plurality of non-conductive threads, the conductive threads being interlaced with the non-conductive threads at predetermined intervals and interlacing angles to provide a pattern of connection locations, the connection locations being located at regular intervals on at least one of a top face and a bottom face of the woven fabric, the conductive threads being woven into the fabric to form wiring and individually addressable electrodes, the wiring and individually addressable electrodes being arranged in a hexagonal pixel layout, and the wiring and individually addressable electrodes being configured to connect with sensors, actuators, and communication devices, wherein at least two of the conductive threads provide electrical muscle stimulation signals applied through skin contact electrodes supported by the woven fabric where the electrical muscle stimulation signals are applied to cause involuntary muscle contractions.

11. The wearable electronic fabric according to claim 10; wherein the conductive threads are insulated with a conductive core.

12. The wearable electronic fabric according to claim 10; wherein the conductive threads include at least one conductive thread having a semiconductor composition.

13. The wearable electronic fabric according to claim 10, wherein at least two of the conductive threads carry an electrical muscle stimulation signal to apply an electrical signal to at least one of muscles and nerves of a user to induce involuntary muscle contractions to cause movement and change a position of at least one body part of the user; wherein the electrical signal is applied as a the first sensory cues to the user to cause the involuntary muscle contraction to cause movement and change the position of the at least one body part of the user in response to the electrical signal applied to the user.

14. A wearable electronic garment comprising a fabric formed from interlaced threads, wherein the fabric includes a plurality of conductive threads interlaced at predetermined intervals and angles to provide a pattern of connection locations, the connection locations being located at regular intervals on at least one of the top and the bottom face of the fabric, and the conductive threads being interlaced in the warp and weft threads so that at the regular intervals a connection area is disposed having a plurality of conductive threads providing a ground connection portion, a power connection portion, a data-in connection portion, a data-out connection portion, a first electrical apply connection, and a second electrical apply connection, where the regular intervals and interlacing angles of the warp and weft of the interlaced threads disposes the conductive threads so that the respective connection portions are each located at a corresponding vertices of a connection area located at the regular intervals, and a plurality of connection areas are located at the regular intervals on at least one of the top and the bottom face of the fabric, wherein the garment further includes individually addressable skin contact electrodes supported on the fabric of the garment.

15. The wearable electronic according to claim 14, wherein at least two of the conductive threads carry an electrical muscle stimulation signal to apply an electrical signal to at least one of muscles and nerves of a user to induce involuntary muscle contractions to cause movement and change a position of at least one body part of the user; wherein the electrical signal is applied as the first sensory cues to the user to cause the involuntary muscle contraction to cause movement and change the position of the at least one body part of the user in response to the electrical signal applied to the user.

16. The wearable electronic according to claim 14, further comprising a display for providing visual sensory cues to the user to provide a virtual visual indication to the user of a change in position of the at least one body part so that the change in position of the at least one body part is virtually visually indicated in synchronization with the change in the position of the at least one body part.

17. The wearable electronic according to claim 16, wherein the video display device comprises at least one an augmented or virtual reality headset, a computer monitor, a television, a smart phone display or a personal information device display.

18. The wearable electronic according to claim 14, wherein at least one body part is at least one leg of the user; wherein a visual sensory cue includes a visual scene related to riding of a bicycle; and wherein an applied electrical signal causes an induced movement of at least one leg synchronized with the visual sensory cue for building up muscle memory to strengthen the user's brain and nervous functions that control the change in the position of the at least one leg.

19. The wearable electronic according to claim 18, further comprising a sensory cue generator for generating a second sensory cue capable of being perceived by the user, the second sensory cue being dependent on at least one of a recorded non-biometric data and a the recorded biometric data, the second sensory cue being effective for stimulating at least a second processing area of the brain of the user, the second sensory cues being synchronized with a the visual sensory cues so that the second processing area is stimulated with the second sensory cue in synchronization with the visual sensory cue stimulating a visual processing area, wherein the synchronized stimulation of the visual processing area and the second processing area is effective for building up muscle memory to strengthen the user's brain and nervous functions.

\* \* \* \* \*